US011958754B2

(12) United States Patent
Nockemann et al.

(10) Patent No.: US 11,958,754 B2
(45) Date of Patent: Apr. 16, 2024

(54) ENHANCED SEPARATION OF RARE EARTH METALS

(71) Applicant: Seren Technologies Limited, Redcar (GB)

(72) Inventors: Peter Nockemann, Belfast (GB); Donnacha Brolly, Cleveland (GB); Ena Bradley, Cleveland (GB); Eadaoin Mccourt, Cleveland (GB)

(73) Assignee: Seren Technologies Limited, Redcar (GB)

( * ) Notice: Subject to any disclaimer, the term of this patent is extended or adjusted under 35 U.S.C. 154(b) by 766 days.

(21) Appl. No.: 17/252,257

(22) PCT Filed: Jun. 14, 2019

(86) PCT No.: PCT/GB2019/051661
§ 371 (c)(1),
(2) Date: Dec. 14, 2020

(87) PCT Pub. No.: WO2019/239150
PCT Pub. Date: Dec. 19, 2019

(65) Prior Publication Data
US 2021/0269322 A1     Sep. 2, 2021

(30) Foreign Application Priority Data

Jun. 15, 2018 (GB) .................................... 1809815

(51) Int. Cl.
*C01F 17/17* (2020.01)
*C01F 17/271* (2020.01)
(Continued)

(52) U.S. Cl.
CPC ............ *C01F 17/17* (2020.01); *C01F 17/271* (2020.01); *C07D 233/61* (2013.01);
(Continued)

(58) Field of Classification Search
CPC .......... C01F 17/17; C01F 17/271; C22B 3/28; C22B 59/00; C07D 233/61; C07F 9/5407; C07F 9/5442
(Continued)

(56) References Cited

U.S. PATENT DOCUMENTS

2016/0348213 A1   12/2016  Sun et al.

FOREIGN PATENT DOCUMENTS

CN         106544505         3/2017
CN         107760888         3/2018
(Continued)

OTHER PUBLICATIONS

Bogart et al., "An Operationally Simple Method for Separating the Rare-Earth Elements Neodymium and Dysprosium," Angew. Chem. Int. Ed., 2015; 54: pp. 8222-8225.
(Continued)

*Primary Examiner* — Anita Nassiri-Motlagh
(74) *Attorney, Agent, or Firm* — Arnall Golden Gregory LLP

(57) ABSTRACT

A method for extracting a rare earth metal from a mixture of one or more rare earth metals, said method comprising contacting an acidic solution of the rare earth metal with a composition which comprises an ionic liquid to form an aqueous phase and a non-aqueous phase into which the rare earth metal has been selectively extracted, wherein the ionic liquid has the formula $[Ca^+][X']$, where $[X']$ represents a phosphinate anion.

20 Claims, 4 Drawing Sheets

(51) Int. Cl.

| | |
|---|---|
| *C07D 233/61* | (2006.01) |
| *C07F 9/54* | (2006.01) |
| *C22B 3/26* | (2006.01) |
| *C22B 3/28* | (2006.01) |
| *C22B 59/00* | (2006.01) |

(52) U.S. Cl.
 CPC .......... *C07F 9/5407* (2013.01); *C07F 9/5442* (2013.01); *C22B 3/26* (2021.05); *C22B 3/28* (2021.05); *C22B 59/00* (2013.01)

(58) Field of Classification Search
 USPC ........................................................ 423/21.5
 See application file for complete search history.

(56) References Cited

FOREIGN PATENT DOCUMENTS

| | | |
|---|---|---|
| GB | 2351285 | 12/2000 |
| GB | 2560871 | 10/2018 |
| TW | 201831698 | 9/2018 |
| WO | WO-2007/071028 | 6/2007 |
| WO | WO-2015/106324 | 7/2015 |
| WO | WO-2017/096470 | 6/2017 |
| WO | WO-2018/109483 | 6/2018 |

OTHER PUBLICATIONS

Yuan et al., "Solvent Extraction of Lanthanides in Aqueous Nitrite Media by Cyanex 302," Acta Metallurgica Sinica, 1995; 8(1): pp. 10-14.

Dong et al., "The development of an extraction strategy based on EHEHP-type functional ionic liquid for heavy rare earth element separation", Hydrometallurgy, 2015; 157: pp. 256-260.

Dupont et al., "Rare-earth recycling using a functionalized ionic liquid for the selective dissolution and revalorization of $Y_2O_3$:$Eu^{3+}$ from lamp phosphor waste", Green Chemistry, 2015; 17: pp. 856-868.

Dupont et al., "Recycling of rare earths from NdFeB magnets using a combined leaching/extraction system based on the acidity and thermomorphism of the; ionic liquid [Hbet][Tf2N]", Green Chemistry, 2015; 17: pp. 2150-2163.

English translation of Search Report of TW Patent Application No. 108120736 completed Feb. 21, 2023.

English translation of Search Report of TW Patent Application No. 108120754 completed Jan. 13, 2023.

Fryxell et al., "Design and synthesis of chelating diamide sorbents for the separation of lanthanides", Inorganic Chemistry Communications, 2011; 14: pp. 971-974.

Gupta et al., "Extractive Metallurgy of Rare Earths", CRC, New York, 2005: pp. 1-484.

International Search Report and Written Opinion issued in related International Application No. PCT/GB2019/051660, dated Sep. 3, 2019.

Naik et al., "Ionic Liquid Complexes for Metal Extractions and Biphasic Catalysis", ACS Symposium Series, 2009; vol. 1030, 17, pp. 239-253.

Search Report issued in related United Kingdom Application No. GB1809813.7, dated Jan. 29, 2019.

Song et al., "Extraction and separation of rare earths from chloride medium with mixtures of 2-ethylhexylphosphonic acid mono-(2-ethylhexyl) ester and sec-nonylphenoxy acetic acid", J. Chem. Technol. Biotechnol., 2009, 84: pp. 1798-1802. Abstract Only.

Swain et al., "Competitive extraction of lanthanides by solvent extraction using Cyanex 272: Analysis, classification and mechanism", Separation and Purification Technology, 2011; 83: pp. 82-90. Abstract Only.

Search Report issued in related United Kingdom Application No. GB1809815.2, dated Feb. 1, 2019.

International Search Report and Written Opinion issued in related International Application No. PCT/GB2019/051661, dated Aug. 21, 2019.

Liu et al., "Application and Perspective of Ionic Liquids on Rare Earths Green Separation", Separation Science and Technology, 2012; 47(2): pp. 223-232.

ENHANCED SEPARATION OF RARE EARTH METALS

The present invention relates to the extraction and separation of rare earth metals. In particular, the present invention relates to the extraction and separation of rare earth metals using specifically designed ionic liquids.

Rare earth metals, which include the lanthanides (La to Lu), Y, and Sc, have unique physicochemical properties which make them crucial components of numerous high-tech products and environmental technologies such as wind mills, LCD/LED displays, phosphors, magnet drives (hard disk), and others. These applications demand a continuous supply of high purity rare earth metals to the industries, which is currently met by mining and processing the natural ores of these metals. However, there are concerns that the exponentially increasing demand of these metals will surpass the supply in coming years and therefore, it has become attractive to explore other secondary sources of these valuable metals. One such source is the recovery of rare earth metals from end-of-life and manufacturing wastes materials (often referred to as "urban mining"), which, though quite challenging, can potentially provide a continuous supply of the rare earth metals. One of most important requirements of urban mining is the development of cost effective and robust separation processes/technologies which allow selective and efficient separation of rare earth metals from each other (intra-group separation) to provide high purity rare earth metals.

During the last five decades various processes such as liquid-liquid extraction (e.g. Rhône-Poulenc process), ion exchange, and precipitation have been developed. Among the various available technologies, liquid-liquid extraction has been found to be the most suitable commercial process owing to its scalability, adaptability, and recyclability. Additionally, the liquid-liquid extraction processes used to date employ commercial organophosphorus extractants which do not possess specific selectivity for individual rare earth metals, thereby leading to a number of stages to separate rare earth metals from each other (see Table 1). Furthermore, additional processing steps are generally required to recover the rare earth metal in high purity. These factors lead to manifold increase in processing costs thereby putting strain on overall costing of consumer products. Also, most employed methods for the separation of rare earth metals necessitate the use of organic solvents, which due to their toxicity, volatility and flammability are not considered environmentally friendly. Some of the currently used industrial liquid-liquid extraction processes available for intra-group separation of rare earth metals (e.g. separation of dysprosium from neodymium) are compared in Table 1.

The separation factor for an individual rare earth metal pair is expressed as the ratio of the distribution ratios ($D_M$) of the rare earth metals, where the distribution ratio of an individual rare earth metal is determined as the ratio of its concentration in the non-aqueous phase to that in the aqueous phase i.e. $D_M=[M]_{N-Aq}/[M]A_q$. For example, the separation factor of Dysprosium with respect to Neodymium=$D_{Dy}/D_{Nd}$.

TABLE 1

Comparison of the separation factors of commonly used REM extractants.

| Liquid-liquid extraction | Major component | Separation factor | Reference |
|---|---|---|---|
| HDEHP process | Bis-(2-ethylhexyl)-phosphoric acid | 41.5 (Dy/Nd) | C. K. Gupta, N. Krishnamurthy, Extractive Metallurgy of Rare Earths, CRC, New York, 2005, pp. 1-484. |
| Cyanex 272 process | Bis-(2,4,4-trimethylpentyl) phosphinic acid | 1.36 (Dy/Nd) | B. Swain, E.O. Otu, Separation and Purification Technology, 83, (2011), 82-90 |
| Cyanex 302 process | Bis-(2,4,4-trimethylpentyl)-monothiophosphinic acid | 239.3 (Dy/Nd) | M. Yuan, A. Luo, D. Li, Acta Metall. Sin. 1995, 8, 10-14. |
| Synergist process | 2-ethylhexylphosphonic acid mono-(2-ethylhexyl)ester; sec-nonylphenoxy acetic acid | 1.17 (Dy/Nd) | N. Song, S. Tong, W. Liu, Q.Jia, W.Zhoua and W.Liaob, J. Chem. Technol. Biotechnol., 2009, 84, 1798-1802. |

Another of the most commonly used organophosphorous extractants, P507 (2-ethylhexyl phosphoric acid mono(2-ethylhexyl) ester), also gives low separation factors, with the selectivity for heavy rare earth metals generally being lower than for light rare earth metals (e.g. Tm/Er (3.34), Yb/Tm (3.56), and Lu/Yb (1.78)). Another significant deficiency of many common rare earth metal extractants such as P507 is that it is difficult to strip heavy rare earth metals completely, especially for Tm(III), Yb(III), and Lu(III), even at higher acidity. Low selectivity for rare earth metals results in too many stages required for effective separation, the low extractability of rare earth metals demanding the use of higher concentrations of the extractant. The production of organophosphorous extractants also requires complicated synthetic procedures starting from hazardous starting materials and the stability and recyclability of these extractants is limited. Emulsification and leaching of extractants has been identified as another common problem.

A chelating diamide extractant attached to a silica support was reported by Fryxell et al. for the separation of lanthanides (*Inorganic Chemistry Communications*, 2011, 14, 971-974). However, this system was unable to extract rare earth metals under acidic conditions (pH<5) and crucially showed very low uptake and separation factors between rare earth metals.

Ionic liquids have also been used as potential extractants for rare earth metals. Binnemans et al. reported the extraction of Nd and Dy or Y and Eu from mixtures of transition metal compounds with a betainium bis(trifluoromethylsulfonyl)imide ionic liquid (*Green Chemistry*, 2015, 17, 2150-2163; *Green Chemistry*, 2015, 17, 856-868). However, this system was unable to selectively perform intra-group separation between rare earth metals.

Chai et al. reported the use of an ionic liquid based on 2-ethylhexyl phosphonic acid mono(2-ethylhexyl) ester (P507) with a trioctylmethylammonium cation for separation of rare earth metals (*Hydrometallurgy*, 2015, 157(C), 256-260). In this case only low distribution factors and separation factors were observed, indicating a lack of extractability and selectivity. In addition, during recovery of the rare earth metal from the ionic liquid, the acid added will decompose the acid-base pair ionic liquid, which must then be regenerated by metathesis.

Separation of Nd and Dy was reported by Schelter et al., whereby separation was achieved by precipitation using a tripodal nitroxide ligand to form Nd and Dy complexes with differing solubilities in benzene. However, precipitation is not considered to be a commercially viable process and, in addition, the process requires the use of specific rare earth metal precursors and an inert, moisture-free environment, which is highly impractical for commercial scale up. This method also relies on the use of benzene to achieve high separation, which is a very toxic solvent.

Therefore, there is a need for the development of effective processes that enhance separation selectivity and extractability, whilst minimizing environmental pollution.

By using an ionic liquid having a cation comprising particular features, rare earth metals may be extracted and separated from each other with increased selectivity and extractability in comparison to known methods using different extractants. It has now been found that, by using a particular anion in the ionic liquid, the levels of extractability may be increased yet further. As the method uses an ionic liquid, the extractant can also provide decreased volatility and flammability, potentially leading to safer and more environmentally friendly rare earth metal extraction.

Thus, in a first aspect, the present invention provides a method for extracting a rare earth metal from a mixture of one or more rare earth metals, said method comprising contacting an acidic solution of the rare earth metal with a composition which comprises an ionic liquid to form an aqueous phase and a non-aqueous phase into which the rare earth metal has been selectively extracted, wherein the ionic liquid has the formula:

in which:

[Cat$^+$] represents a cationic species having the structure:

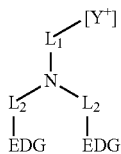

where: [Y$^+$] comprises a group selected from ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium and uronium groups;

each EDG represents an electron donating group; and

L$_1$ represents a linking group selected from C$_{1-10}$ alkanediyl, C$_{2-10}$ alkenediyl, C$_{1-10}$ dialkanylether and C$_{1-10}$ dialkanylketone groups;

each L$_2$ represents a linking group independently selected from C$_{1-2}$ alkanediyl, C$_2$ alkenediyl, C$_{1-2}$ dialkanylether and C$_{1-2}$ dialkanylketone groups; and

[X$^-$] represents an phosphinate anion.

The term "ionic liquid" as used herein refers to a liquid that is capable of being produced by melting a salt, and when so produced consists solely of ions. An ionic liquid may be formed from a homogeneous substance comprising one species of cation and one species of anion, or it can be composed of more than one species of cation and/or more than one species of anion. Thus, an ionic liquid may be composed of more than one species of cation and one species of anion. An ionic liquid may further be composed of one species of cation, and one or more species of anion. Still further, an ionic liquid may be composed of more than one species of cation and more than one species of anion.

The term "ionic liquid" includes compounds having both high melting points and compounds having low melting points, e.g. at or below room temperature. Thus, many ionic liquids have melting points below 200° C., particularly below 100° C., around room temperature (15 to 30° C.), or even below 0° C. Ionic liquids having melting points below around 30° C. are commonly referred to as "room temperature ionic liquids" and are often derived from organic salts having nitrogen-containing heterocyclic cations. In room temperature ionic liquids, the structures of the cation and anion prevent the formation of an ordered crystalline structure and therefore the salt is liquid at room temperature.

Ionic liquids are most widely known as solvents. Many ionic liquids have been shown to have negligible vapour pressure, temperature stability, low flammability and recyclability. Due to the vast number of anion/cation combinations that are available it is possible to fine-tune the physical properties of the ionic liquid (e.g. melting point, density, viscosity, and miscibility with water or organic solvents) to suit the requirements of a particular application.

Typically, when rare earth metals are extracted from sources such as ores or waste materials, the resulting product is a mixture of rare earth metals dissolved in an aqueous acidic solution. In the method according to the present invention, rare earth metals may be selectively extracted directly from an aqueous acidic feed, negating the need to apply significant processing to the feed prior to extraction.

It will be appreciated that in order to form an aqueous phase and a non-aqueous phase when contacted with the acidic solution, the composition comprising an ionic liquid will be sufficiently hydrophobic such that a phase separation will occur between the aqueous solution and the composition.

By the use of the composition comprising an ionic liquid as defined according to the first aspect, it has been surprisingly found that increased selectivity and extractability may be obtained in the extraction of rare earth metals from an acidic solution. The combination of high extractability (indicated by distribution ratio) and selectivity (indicated by separation factors) is key to a commercially effective separation process because the number of separation stages necessary to produce a product may be reduced without sacrificing purity.

For example, according to the method of the present invention, mixtures of dysprosium and neodymium may be separated with a selectivity (separation factor) of over 1000:1 in a single contact. This represents a substantial increase over known systems as reported in Table 1.

Without wishing to be bound by any particular theory, it is believed that the presence of the central nitrogen donor atom in the ionic liquid allows for differing binding strengths to different rare earth metals as a result of differing ionic radii due to lanthanide contraction. In this way, some rare earth metals are preferentially bound by the hydrophobic ionic liquid extractant, which results in effective intra-group separation of the rare earth metals. It is believed that the arrangement of this variable nitrogen binding as part of an ionic liquid provides the particularly effective extraction of rare earth metals described herein.

Nonetheless, it will be appreciated that the ionic liquid comprising a nitrogen donor, whilst discriminating between different rare earth metals, must have additional electron donating groups appended in order to provide sufficient extractability.

Preferably, the method further comprises recovering the rare earth metal from the non-aqueous phase. This recovery may be performed using any suitable means, however it is preferred that the rare earth metal is recovered from the non-aqueous phase by stripping with an acidic stripping solution.

It will be appreciated that the acidic stripping solution may be any acidic solution which liberates the rare earth metal from the ionic liquid. In most embodiments, the acidic stripping solution will be an aqueous acidic stripping solution and the acid will substantially remain in the aqueous phase on contact with the ionic liquid. Preferably, the acidic stripping solution comprises an aqueous hydrochloric acid or nitric acid solution.

The stripping of the rare earth metal may be conducted in any suitable manner. Preferably, the ionic liquid is contacted with an acidic stripping solution for 2 or more stripping cycles to completely strip the rare earth metal, more preferably 2 or 3 stripping cycles are used. In some embodiments, a single stripping cycle may be used. A "stripping cycle" as referred to herein will typically comprise contacting the acidic stripping solution with the composition, equilibrating for an amount of time, for example 5 to 30 minutes, and separating the aqueous and organic phases. A second cycle may be conducted by contacting the composition with another acidic stripping solution substantially free of rare earth metals.

One advantage of the ionic liquid extractant as described in relation to the first aspect is that the rare earth metal may be stripped from the ionic liquid at a relatively high pH. This saves costs associated with both the amount and the strength of acid needed to strip the rare earth metals from the ionic liquid and the equipment necessary to handle such strong acids. In addition, it is possible to completely strip rare earth metals from the ionic liquid at a relatively high pH, whilst for many known extractants such as P507 it is difficult to completely strip heavy rare earth metals (e.g. Tm(III), Yb(III), Lu(III)) even at low pH.

Thus, the acidic stripping solution preferably has a pH of 0 or higher. In preferred embodiments, the acidic stripping solution has a pH of 1 or lower.

In preferred embodiments, the method comprises extracting a rare earth metal from a mixture of two or more rare earth metals. Preferably, the acidic solution comprises a first and a second rare earth metal, and the method comprises:
  (a) preferentially partitioning the first rare earth metal into the non-aqueous phase.

Preferably, the method further comprises, in step (a), separating the non-aqueous phase from the acidic solution; and
  (b) contacting the acidic solution depleted of the first rare earth metal with the composition which comprises an ionic liquid, and optionally recovering the second rare earth metal therefrom.

In some preferred embodiments the first rare earth metal is recovered from the non-aqueous phase in step (a), and said non-aqueous phase is recycled and used as the composition in step (b).

It will be appreciated that, because the extractability (distribution factor) for a particular rare earth metal varies with pH, it may be preferred to extract different rare earth metals at different pH levels. For example, the acidic solution may have a lower pH in step (a) in comparison to that in step (b). Preferably, the acidic solution has a pH of less than 3.5 in step (a), and the acidic solution has a pH of greater than 3.5 in step (b). Typically, 2 or 3 extraction cycles will be performed at a particular pH. Although the above embodiment describes extraction in only two different pH values, it will be appreciated that a separation of rare earth metals will usually be conducted across a range of pH values, with a gradual increase in pH and multiple extraction steps. For example, where three or more rare earth metals are separated, several separation steps may be conducted in across a particular pH range, for example from pH 1 to 4.

The acidic solution from which the rare earth metal is extracted may have any suitable pH. Preferably, the rare earth metal is extracted at a pH of more than 1, more preferably at a pH of from 2 to 4.

The pH level of the acidic solution of the rare earth metal may be adjusted in any suitable way, as is well known to those skilled in the art. For example, the pH level of the acidic solution may be altered by the addition of acid scavengers such as mildly alkaline solutions including sodium carbonate, sodium bicarbonate, ammonia, $CO_2$, amines or alcohols.

The above embodiments refer to the separation of a particular rare earth metal from another directly from the acidic solution of the rare earth metal at varying pH levels. However, it will be understood that any suitable extraction sequence may be used to separate rare earth metals. For example, two or more rare earth metals may be extracted from the acidic solution to the non-aqueous phase simultaneously at a higher pH, followed by back-extraction of the non-aqueous phase with acidic solutions having a lower pH to separate individual rare earth metals. Thus, all or only some of the rare earth metals present in the acidic solution may initially be extracted from the acidic solution using the composition comprising the ionic liquid.

It will be appreciated that the separation of certain pairs of rare earth metals are of particular importance due to their simultaneous recovery from valuable waste materials. For example, Nd and Dy are widely used in permanent magnets for numerous applications such as hard disks, MRI scanners, electric motors and generators. La and Eu are also an important pair due to their common use in lamp phosphors, other phosphors include Y and Eu (YOX phosphors); La, Ce and Tb (LAP phosphors); Gd, Ce and Tb (CBT phosphors); and Ce, Tb (CAT phosphors).

Thus, in preferred embodiments, the first rare earth metal is dysprosium, and the second rare earth metal is neodymium. In other preferred embodiments, the first rare earth metal is europium, and the second rare earth metal is lanthanum. In yet other preferred embodiments, the first rare earth metal is terbium, and the second rare earth metal is cerium.

The composition may be contacted with the acidic solution in any suitable manner and in any suitable ratio such that exchange of rare earth metals is achieved between the aqueous and non-aqueous phases.

The composition is preferably added to the acidic solution in a volume ratio of from 0.5:1 to 2:1, preferably 0.7:1 to 1.5:1, more preferably 0.8:1 to 1.2:1, for example 1:1. Nonetheless, it will be appreciated that the volume ratio will vary depending on the manner in which the acidic solution is contacted with the composition comprising the ionic liquid.

Preferably, prior to contacting the composition with the acidic solution of the rare earth metal the composition is equilibrated with an acidic solution having the same pH as the acidic solution of the rare earth metal. In this way, the mixture of the composition and the acidic solution will generally remain at the desired pH level during the extraction.

The composition may be contacted with the acidic solution of the rare earth metal under any conditions suitable for extracting the rare earth metal.

It will be appreciated that the temperature employed during contacting of the acidic solution with the composition comprising the ionic liquid may be any suitable temperature and may vary according to the viscosity of the composition comprising the ionic liquid. For example, where a higher viscosity composition is used, a higher temperature may be necessary in order to obtain optimal results.

Preferably, the acidic solution is contacted with the composition at ambient temperature, i.e. without external heating or cooling. It will nonetheless be appreciated that temperature changes may naturally occur during the extraction as a result of contacting the composition with the acidic solution.

The composition may be contacted with the acidic solution of the rare earth metal for any length of time suitable to facilitate extraction of the rare earth metal into the non-aqueous phase. Preferably, the length of time will be such that an equilibrium is reached and the proportions of rare earth metal in the aqueous and non-aqueous phases are constant. In preferred embodiments, the method comprises contacting the acidic solution of the rare earth metal and the composition for from 1 to 40 minutes, preferably from 5 to 30 minutes.

Preferably, the method comprises contacting and physically mixing the acidic solution of the rare earth metal and the composition. Such mixing will usually speed up extraction of the rare earth metal. Any suitable apparatus may be used to achieve this and mixing apparatus is well known in the art. For example, the mixture may be mixed using an agitator or stirrer. The mixing apparatus may comprise equipment specifically designed for multi-phase mixing such as high shear devices. Alternatively, mixing may comprise shaking the mixture, for example, using a wrist action shaker.

The separation of the aqueous and non-aqueous phases may be performed by any suitable method, for example by use of small scale apparatus such as a separating funnel or Craig apparatus. It will be appreciated that the phases will normally be allowed to settle prior to separation. Settling may be under gravity or preferably accelerated by the use of additional equipment such as centrifuge. Alternatively, aqueous and non-aqueous phases may be separated by the use of equipment which both contacts and separates the phases, for example a centrifugal extractor, a pulsed column, or a combined mixer-settler.

It will be understood that in order to extract or separate some rare earth metals, multiple extractions and separations may be performed. This may involve multiple extractions of the acidic solution of the rare earth metal with the composition or multiple back-extractions of the non-aqueous phase with an aqueous acidic solution. In accordance with the present invention, fewer steps are required to separate rare earth metals due to the ionic liquid extractant giving separation factors and distribution ratios above those typically found in previous systems.

The term electron donating group (EDG) as used herein will be understood to include any group having a pair of electrons available to form a coordinate bond with an acceptor. In particular, it will be appreciated that an electron donating group, as defined herein, refers to groups having an available pair of electrons able to coordinate to a rare earth metal to form a metal-ligand complex. It will also be understood that the EDGs will typically have a single atom from which the electrons are donated to form a bond. However, electrons may alternatively be donated from one or more bonds between atoms, i.e. EDG may represent a ligand with a hapticity of 2 or more.

It will be understood that the arrangement of the EDGs and the linkers $L_2$ will be such that the EDGs and the central nitrogen atom are able to coordinate to a rare earth metal simultaneously.

Preferably, when the nitrogen linking $L_1$ to each $L_2$ and one of the EDG both coordinate to a metal, the ring formed by the nitrogen, $L_2$, the EDG and the metal is a 5 or 6 membered ring, preferably a 5 membered ring.

In preferred embodiments, [Y$^+$] represents an acyclic cation selected from:

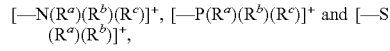

wherein: $R^a$, $R^b$ and $R^c$ are each independently selected from optionally substituted $C_{1-30}$ alkyl, $C_{3-8}$ cycloalkyl and $C_{6-10}$ aryl groups.

In other preferred embodiments, [Y$^+$] represents a cyclic cation selected from:

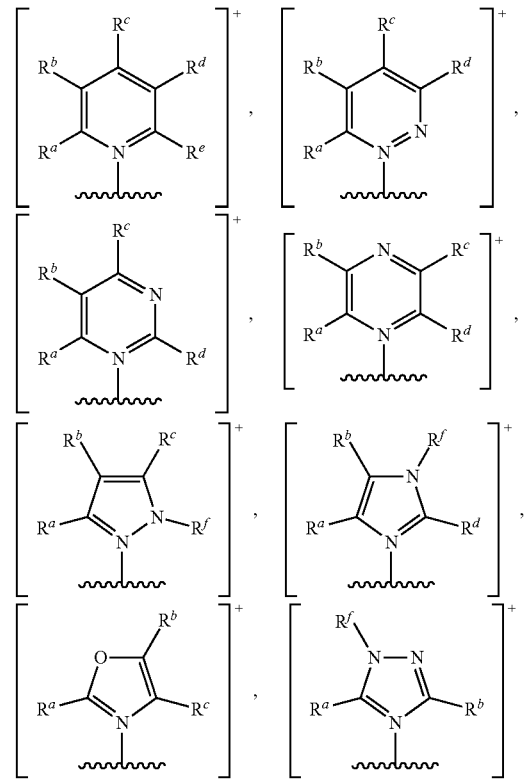

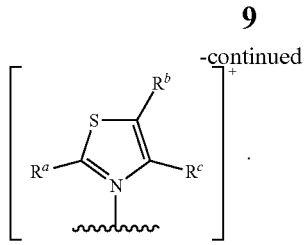

wherein: $R^a$, $R^b$, $R^c$, $R^d$, $R^e$ and $R^f$ are each independently selected from:

hydrogen and optionally substituted $C_{1-30}$ alkyl, $C_{3-8}$ cycloalkyl and $C_{6-10}$ aryl groups, or any two of $R^a$, $R^b$, $R^c$, $R^d$ and $R^e$ attached to adjacent carbon atoms form an optionally substituted methylene chain $—(CH_2)_q—$ where q is from 3 to 6.

Suitably, in preferred embodiments, at least one of $R^a$, $R^b$, $R^c$, $R^d$, $R^e$ and $R^f$ is a $C_{1-5}$ alkyl group substituted with $—CO_2R^x$, $—OC(O)R^x$, $—CS_2R^x$, $—SC(S)R^x$, $—S(O)OR^x$, $—OS(O)R^x$, $—NR^xC(O)NR^yR^z$, $—NR^xC(O)OR^y$, $—OC(O)NR^yR^z$, $—NR^xC(S)OR^y$, $—OC(S)NR^yR^z$, $—NR^xC(S)SR^y$, $—SC(S)NR^yR^z$, $—NR^xC(S)NR^yR^z$, $—C(O)NR^yR^z$, $—C(S)NR^yR^z$, wherein $R^x$, $R^y$ and $R^z$ are independently selected from hydrogen or $C_{1-6}$ alkyl.

In another preferred embodiment of the invention, [Y⁺] represents a saturated heterocyclic cation selected from cyclic ammonium, 1,4-diazabicyclo[2.2.2]octanium, morpholinium, cyclic phosphonium, piperazinium, piperidinium, quinuclidinium, and cyclic sulfonium.

Preferably, [Y⁺] represents a saturated heterocyclic cation having the formula:

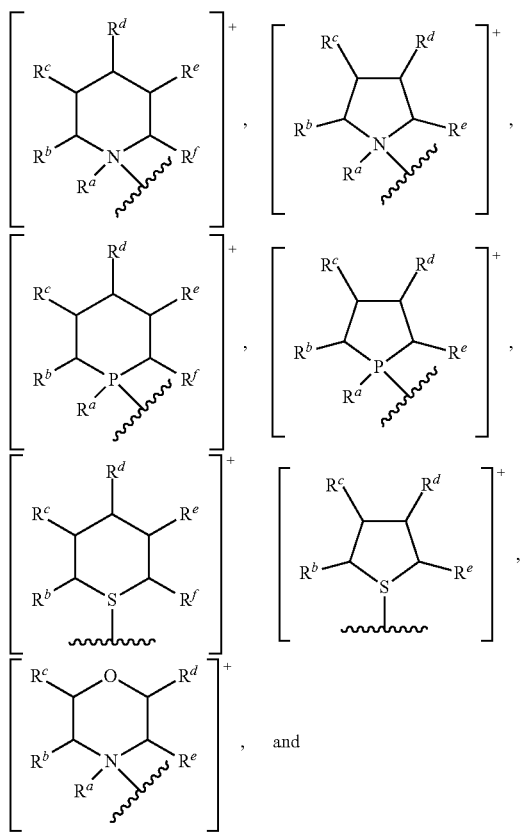

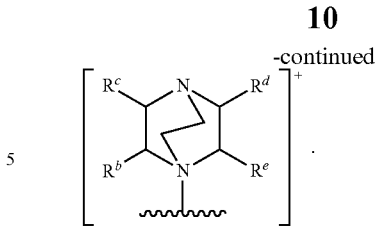

wherein: $R^a$, $R^b$, $R^c$, $R^d$, $R^e$ and $R^f$, are as defined above.

Preferably, at least one of $R^a$, $R^b$, $R^c$, $R^d$, $R^e$ and $R^f$ is $C_{1-3}$ alkyl group substituted with $—CO_2R^x$, $—C(O)NR^yR^z$, wherein $R^x$, $R^y$ and $R^z$ are each independently selected from $C_{3-6}$ alkyl.

More preferably, at least one of $R^a$, $R^b$, $R^c$, $R^d$, $R^e$ and $R^f$ represents a group selected from:

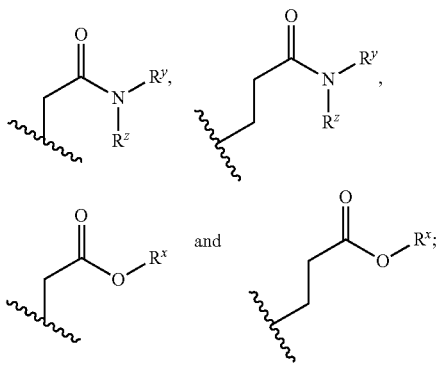

wherein $R^y=R^z$, and wherein $R^x$, $R^y$ and $R^z$ are each selected from $C_{3-6}$ alkyl, preferably $C_4$ alkyl, for example i-Bu.

Yet more preferably, at least one of $R^a$, $R^b$, $R^c$, $R^d$, $R^e$ and $R^f$ represents a group selected from:

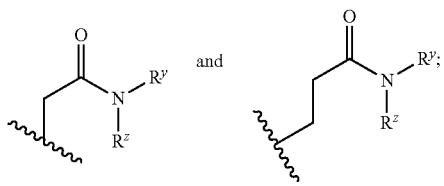

wherein $R^y=R^z$, and wherein $R^y$ and $R^z$ are selected from $C_{3-6}$ alkyl, preferably $C_4$ alkyl, for example i-Bu.

In preferred embodiments, one of $R^a$, $R^b$, $R^c$, $R^d$, $R^e$ and $R^f$ is a substituted $C_{1-5}$ alkyl group, and the remainder of $R^a$, $R^b$, $R^c$, $R^d$, $R^e$ and $R^f$ are independently selected from H and unsubstituted $C_{1-5}$ alkyl groups, preferably the remainder of $R^a$, $R^b$, $R^c$, $R^d$, $R^e$ and $R^f$ are H.

Preferably, [Y⁺] represents a cyclic cation selected from:

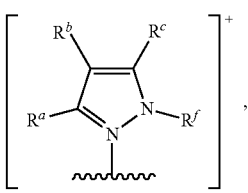

-continued

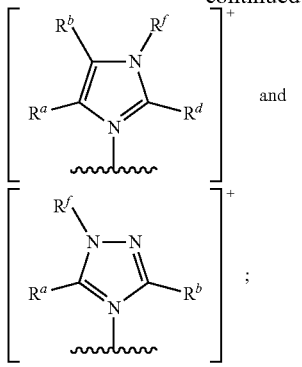

and

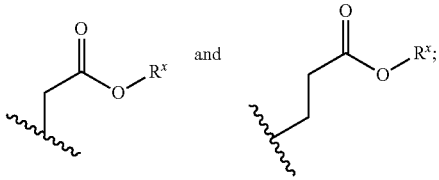

more preferably [Y⁺] represents the cyclic cation:

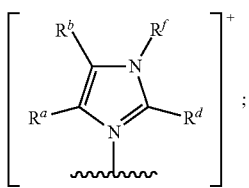

preferably wherein $R^f$ is a substituted $C_{1-5}$ alkyl group, and the remainder of $R^a$, $R^b$, $R^c$, $R^d$, $R^e$ and $R^f$ are independently selected from H and unsubstituted $C_{1-5}$ alkyl groups.

In preferred embodiments, $L_1$ represents a linking group selected from $C_{1-10}$ alkanediyl and $C_{1-10}$ alkenediyl groups, more preferably selected from $C_{1-5}$ alkanediyl and $C_{2-5}$ alkenediyl groups, and most preferably selected from $C_{1-5}$ alkanediyl groups, for example a linking group selected from —$CH_2$—, —$C_2H_4$— and —$C_3H_6$—.

In preferred embodiments, each $L_2$ represents a linking group independently selected from $C_{1-2}$ alkanediyl and $C_2$ alkenediyl groups, preferably selected from $C_{1-2}$ alkanediyl groups, for example independently selected from —$CH_2$— and —$C_2H_4$—.

Each EDG may be any suitable electron donating group able to form a coordinate bond with a rare earth metal to form a metal-ligand complex.

Preferably, each EDG represents an electron donating group independently selected from —$CO_2R^x$, —$OC(O)R^x$, —$CS_2R^x$, —$SC(S)R^x$, —$S(O)OR^x$, —$OS(O)R^x$, —$NR^xC(O)NR^yR^z$, —$NR^xC(O)OR^y$, —$OC(O)NR^yR^z$, —$NR^xC(S)OR^y$, —$OC(S)NR^yR^z$, —$NR^xC(S)SR^y$, —$SC(S)NR^yR^z$, —$NR^xC(S)NR^yR^z$, —$C(O)NR^yR^z$, —$C(S)NR^yR^z$, wherein $R^x$, $R^y$ and $R^z$ are independently selected from H or $C_{1-6}$ alkyl. More preferably, each EDG represents an electron donating group independently selected from —$CO_2R^x$ and —$C(O)NR^yR^z$, wherein $R^x$, $R^y$ and $R^z$ are each independently selected from $C_{3-6}$ alkyl.

In preferred embodiments, each -$L_2$-EDG represents an electron donating group independently selected from:

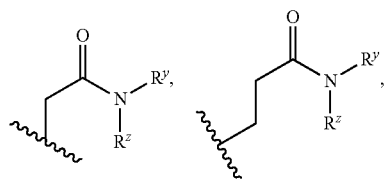

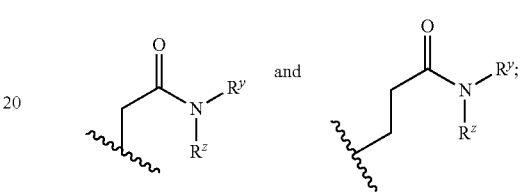

wherein $R^y$=$R^z$, and wherein $R^x$, $R^y$ and $R^z$ are each selected from $C_{3-6}$ alkyl, preferably $C_4$ alkyl, for example i-Bu.

More preferably, each -$L_2$-EDG represents an electron donating group independently selected from:

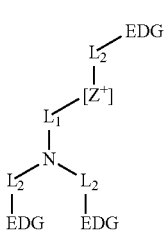

wherein $R^y$=$R^z$, and wherein $R^y$ and $R^z$ are selected from $C_{3-6}$ alkyl, preferably $C_4$ alkyl, for example i-Bu.

In some preferred embodiments, [Cat⁺] represents one or more ionic species having the structure:

where: [Z⁺] represents a group selected from ammonium, benzimidazolium, benzofuranium, benzothiophenium, benzotriazolium, borolium, cinnolinium, diazabicyclo-decenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium and uronium groups.

The anion [X⁻] in the ionic liquid is a phosphinate anion. The use of a phosphinate anion in the ionic liquid is believed to enhance extraction of the rare earth metal during the method of the present invention. Without wishing to be bound by theory, it is believed that the presence of the two oxygen atoms sharing a negative charge may enable the phosphinate anion to effectively complex the rare earth metal, thereby enhancing its partitioning into the non-aqueous phase.

The anion [X−] may represent a phosphinate anion having the structure:

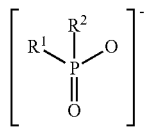

where: $R^1$ and $R^2$ are independently selected from optionally substituted $C_{3-20}$, preferably $C_{4-15}$, and more preferably $C_{6-10}$, hydrocarbyl groups in which up to 3 carbon atoms may be replaced with a heteroatom.

$R^1$ and $R^2$ may be the same or different, but preferably they are the same group.

Optional substituents include one or more groups selected from: fluoro, chloro, bromo, iodo, $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO$_2$, —CO$_2$R$^x$, —OC(O)R$^x$, —C(O)R$^x$, —C(S)R$^x$, —CS·$_2$R$^x$, —SC(S)R$^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S ($C_1$ to $C_6$ alkyl), —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, —NR$^y$R$^z$, or a heterocyclic group, wherein R$^x$, R$^y$ and R$^z$ are independently selected from hydrogen or $C_1$ to $C_6$ alkyl.

Suitable heteroatoms include oxygen and nitrogen.

However, $R^1$ and $R^2$ are preferably independently selected from hydrocarbyl groups, i.e. groups consisting of solely carbon and hydrogen. In other words, the hydrocarbyl groups are preferably unsubstituted and free from heteroatoms. For instance, $R^1$ and $R^2$ may be independently selected from alkyl, cycloalkyl, alkenyl, cycloalkenyl, alkyl-cycloalkyl, cycloalkyl-alkyl, aryl, alkyl-aryl and aryl-alkyl groups.

Most preferably, $R^1$ and $R^2$ are independently selected from alkyl groups. For instance, $R^1$ and $R^2$ may be independently selected from $C_6$ alkyl, $C_7$ alkyl, C alkyl, $C_9$ alkyl and $C_{10}$ alkyl groups.

The alkyl group may be branched or unbranched, though branched alkyl groups are generally preferred. For instance, in one embodiment $R^1$ and $R^2$ are 2,4,4-trimethylpentyl groups and, thus, the anion is bis(2,4,4-trimethylpentyl) phosphinate.

In some embodiments, the composition may consist essentially of the ionic liquid as defined above. However, it is generally preferred that the composition comprise the ionic liquid as defined above in combination with a diluent. Typically, a diluent may be used in order to decrease the viscosity of the composition where the ionic liquid has a high viscosity, which limits its practical use in liquid-liquid extraction. A diluent may also be used to save costs where the diluent is cheaper to produce than the ionic liquid. It will be understood that any diluent added to the composition will be sufficiently hydrophobic so as to allow the separation of the composition and the acidic solution of the rare earth metal into an aqueous and non-aqueous phase. In some embodiments, the diluent may enhance the hydrophobicity of the composition.

Thus, in preferred embodiments, the composition further comprises a lower viscosity ionic liquid. The term "lower viscosity ionic liquid" will be understood to mean that this ionic liquid has a lower viscosity than the ionic liquid extractant described previously. As mentioned, it will be understood that the lower viscosity ionic liquid will be sufficiently hydrophobic so as to allow the separation of the composition and the acidic solution of the rare earth metal into an aqueous and non-aqueous phase. It will also be appreciated that the hydrophobicity may be provided by either of the cation or anion of the lower viscosity ionic liquid, or by both.

By the use of an ionic liquid as a diluent, the decreased volatility and flammability offered by the ionic liquid extractant may be maintained to give a potentially safer and more environmentally friendly rare earth metal extraction process.

In preferred embodiments, the cation of the lower viscosity ionic liquid is selected from ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium and uronium groups.

Preferably the cation of the lower viscosity ionic liquid is selected from phosphonium, imidazolium and ammonium groups.

In some preferred embodiments, the cation of the lower viscosity ionic liquid is selected from:

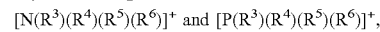

wherein: $R^3$, $R^4$, $R^5$ and $R^6$ are each independently selected from optionally substituted $C_{1-20}$ alkyl, $C_{3-8}$ cycloalkyl and $C_{6-10}$ aryl groups.

In more preferred embodiments, the cation of the lower viscosity ionic liquid is [P($R^3$)($R^4$)($R^5$)($R^6$)]$^+$, wherein $R^3$, $R^4$, $R^5$ are selected from $C_{1-10}$ alkyl, preferably $C_{2-6}$ alkyl, and $R^6$ is selected from $C_{4-20}$ alkyl, preferably $C_{8-14}$ alkyl. For example, the cation of the lower viscosity ionic liquid may be selected from triethyloctyl phosphonium ($[P_{222(8)}]^+$), tributyloctyl phosphonium ($[P_{444(8)}]^+$), trihexyloctyl phosphonium ($[P_{666(8)}]^+$), trihexyldecyl phosphonium ($[P_{666(10)}]^+$), and trihexyltetradecyl phosphonium ($[P_{666(14)}]^+$).

In other more preferred embodiments, the cation of the lower viscosity ionic liquid is [N($R^3$)($R^4$)($R^5$)($R^6$)]$^+$, wherein $R^3$, $R^4$, $R^5$ are selected from $C_{4-14}$ alkyl, preferably $C_{6-10}$ alkyl, and $R^6$ is selected from $C_{1-4}$ alkyl, preferably $C_{1-2}$ alkyl. For example, the cation of the lower viscosity ionic liquid may be selected from trioctylmethyl ammonium, tris(2-ethylhexyl) methyl ammonium, and tetrabutyl ammonium.

In other preferred embodiments, the cation of the lower viscosity ionic liquid is selected from imidazolium cations substituted with one or more $C_{1-20}$ alkyl, $C_{3-8}$ cycloalkyl and $C_{6-10}$ aryl groups, preferably substituted with two $C_{1-10}$ alkyl groups, more preferably substituted with one methyl group and one $C_{1-10}$ alkyl group. For example, the cation of the lower viscosity ionic liquid may be selected from 1-butyl-3-methyl imidazolium, 1-hexyl-3-methyl imidazolium and 1-octyl-3-methyl imidazolium.

Any suitable anionic species may be used as part of the lower viscosity ionic liquid used in the method of the present invention. For instance, the anionic species may be selected from: hydroxides, halides, perhalides, pseudohalides, sulphates, sulphites, sulfonates, sulfonimides, phosphates, phosphites, phosphonates, methides, borates, carboxylates, azolates, carbonates, carbamates, thiophosphates, thiocarboxylates, thiocarbamates, thiocarbonates, xanthates, thiosulfonates, thiosulfates, nitrate, nitrite, tetrafluoroborate, hexafluorophosphate and perchlorate, halometallates, amino acids, borates and polyfluoroalkoxyaluminates.

For example, the anionic species may be selected from:
a) a halide anion selected from: $F^-$, $Cl^-$, $Br^-$, $I^-$;
b) a perhalide anion selected from: $[I_3]^-$, $[I_2Br]^-$, $[IBr_2]^-$, $[Br_3]^-$, $[Br_2Cl]^-$, $[BrCl_2]^-$, $[ICl_2]^-$, $[I_2Cl]^-$, $[Cl_3]^-$;
c) a pseudohalide anion selected from: $[N_3]^-$, $[NCS]^-$, $[NCSe]^-$, $[NCO]^-$, $[CN]^-$; d) a sulphate anion selected from: $[HSO_4]^-$, $[SO_4]^{2-}$, $[R^2OSO_2O]^-$;
e) a sulphite anion selected from: $[HSO_3]^-$, $[SO_3]^{2-}$, $[R^2OSO_2]^-$;
f) a sulfonate anion selected from: $[R^1SO_2O]^-$;
g) a sulfonimide anion selected from: $[(R^1SO_2)_2N]^-$;
h) a phosphate anion selected from: $[H_2PO_4]^-$, $[HPO_4]^{2-}$, $[PO_4]^{3-}$, $[R^2OPO_3]^{2-}$, $[(R^2O)_2PO_2]^-$;
i) a phosphite anion selected from: $[H_2PO_3]^-$, $[HPO_3]^{2-}$, $[R^2OPO_2]^{2-}$, $[(R^2O)_2PO]^-$;
j) a phosphonate anion selected from: $[R^1PO_3]^{2-}$, $[R^1P(O)(OR^2)O]^-$;
k) a methide anion selected from: $[(R^1SO_2)_3C]^-$;
l) a borate anion selected from: [bisoxalatoborate], [bismalonatoborate]tetrakis[3,5-bis(trifluoromethyl)phenyl]borate, tetrakis(pentafluorophenyl)borate;
m) a carboxylate anion selected from: $[R^2CO_2]^-$;
n) an azolate anion selected from: [3,5-dinitro-1,2,4-triazolate], [4-nitro-1,2,3-triazolate], [2,4-dinitroimidazolate], [4,5-dinitroimidazolate], [4,5-dicyano-imidazolate], [4-nitroimidazolate], [tetrazolate];
o) a sulfur-containing anion selected from: thiocarbonates (e.g. $[R^2OCS_2]^-$, thiocarbamates (e.g. $[R^2{}_2NCS_2]^-$), thiocarboxylates (e.g. $[R^1CS_2]^-$), thiophosphates (e.g. $[(R^2O)_2PS_2]^-$), thiosulfonates (e.g. $[RS(O)_2S]^-$), thiosulfates (e.g. $[ROS(O)_2S]^-$);
p) a nitrate ($[NO_3]^-$) or nitrite ($[NO_2]^-$) anion;
q) a tetrafluoroborate ($[BF_4]^-$), hexafluorophosphate ($[PF_6]^-$), hexfluoroantimonate ($[SbF_6]^-$) or perchlorate ($[ClO_4]^-$) anion;
r) a carbonate anion selected from $[CO_3]^{2-}$, $[HCO_3]^-$, $[R^2CO_3]^-$; preferably $[MeCO_3]^-$;
s) polyfluoroalkoxyaluminate anions selected from $[Al(OR^F)_4]^-$, wherein $R^F$ is selected from $C_{1-6}$ alkyl substituted by one or more fluoro groups;
where: $R^1$ and $R^2$ are independently selected from the group consisting of $C_1$-$C_{10}$ alkyl, C aryl, $C_1$-$C_{10}$ alkyl($C_6$)aryl and C aryl($C_1$-$C_{10}$)alkyl each of which may be substituted by one or more groups selected from: fluoro, chloro, bromo, iodo, $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —$NO_2$, —$CO_2R^x$, —$OC(O)R^x$, —$C(O)R^x$, —$C(S)R^x$, —$CS_2R^x$, —$SC(S)R^x$, —$S(O)(C_1$ to $C_6)$alkyl, —$S(O)O(C_1$ to $C_6)$alkyl, —$OS(O)(C_1$ to $C_6)$alkyl, —$S(C_1$ to $C_6)$alkyl, —S—$S(C_1$ to $C_6$ alkyl), —$NR^xC(O)NR^yR^z$, —$NR^xC(O)OR^y$, —$OC(O)NR^yR^z$, —$NR^xC(S)OR^y$, —$OC(S)NR^yR^z$, —$NR^xC(S)SR^y$, —$SC(S)NR^yR^z$, —$NR^xC(S)NR^yR^z$, —$C(O)NR^yR^z$, —$C(S)NR^yR^z$, —$NR^yR^z$, or a heterocyclic group, wherein $R^x$, $R^y$ and $R^z$ are independently selected from hydrogen or $C_1$ to $C_6$ alkyl, wherein $R^1$ may also be fluorine, chlorine, bromine or iodine.

The anionic species in the lower viscosity ionic liquid is preferably a non-coordinating anion. The term "non-coordinating anion" used herein, which is common in the field of ionic liquids and metal coordination chemistry, is intended to mean an anion that does not coordinate with a metal atom or ion, or does so only weakly. Typically, non-coordinating anions have their charge dispersed over several atoms in the molecule which significantly limits their coordinating capacity. This limits the effect interference of the anion with the selective coordination of the cation [Cat$^+$] with the rare earth metal.

Thus, more preferably, the anionic species is a non-coordinating anionic species, e.g. selected from: bistriflimide, triflate, tosylate, perchlorate, $[Al(OC(CF_3)_3)_4]^-$, tetrakis[3,5-bis(trifluoromethyl)phenyl]borate, tetrakis(pentafluorophenyl)borate, tetrafluoroborate, hexfluoroantimonate and hexafluorophosphate anions; and most preferably from bistriflimide and triflate anions.

It will be appreciated that there may be an excess of anions from the lower viscosity ionic liquid in comparison to the ionic liquid extractant. Therefore, it is especially preferred that the anion of the lower viscosity ionic liquid is a non-coordinating anion. For this reason, it is preferable to limit the total amount of halide or pseudohalide anions in the composition. For example, in preferred embodiments the composition comprises less than 25% halide or pseudohalide anions as a proportion of the total anions, preferably less than 20%, more preferably less than 15%, most preferably less than 10%, for example less than 5%. In some embodiments, the composition is substantially free of halide or pseudohalide anions.

It will also be appreciated that mixtures of cations and anions, e.g. mixtures of those cations and ions described above, may be used in the lower viscosity ionic liquid.

The composition may alternatively or additionally further comprise one or more non-ionic liquid diluents. For example, in some preferred embodiments, the composition further comprises one or more organic solvents. It will be understood that suitable organic solvents will include hydrophobic and non-coordinating solvents. The term "non-coordinating solvent" used herein, which is common in the field of metal coordination chemistry, is intended to mean a solvent that does not coordinate with metal atoms or ions, or does so only weakly.

Suitable organic solvents include but are not limited to hydrocarbon solvents such as $C_{1-20}$ alkanes, alkenes or cycloalkanes, aromatic solvents such as toluene or benzene, $C_{6+}$ alcohols such as n-hexanol, etheric solvents such as diethyl ether, dipropyl ether, dibutyl ether and methyl-t-butyl ether, or halogenated solvents such as tetrachloromethane, tetrachloroethane, chloroform, dichloromethane, chlorobenzene, or fluorobenzene. Preferably the organic solvent is a hydrocarbon solvent.

The ionic liquid may be present in the composition in any concentration suitable for extracting rare earth metals and it will be appreciated that this concentration will vary depending on the particular application and pH. In particular, it will be appreciated that for the separation of rare earth metals a competitive separation is desirable. For example the concentration of the ionic liquid should be low enough to avoid the extraction of all rare earth metals present. Therefore, the concentration of the ionic liquid will typically depend on the concentration of rare earth metals to be extracted and the pH at which the separation is conducted.

The composition may comprise the cation and the anion of the ionic liquid in the same amount, e.g. such that the ionic liquid is present in the composition in a concentration of at least 0.001 M, preferably from 0.005 M to 0.01 M.

However, in some embodiments, the cation and the anion of the ionic liquid may be present in the composition in different amounts. For instance, in some embodiments, the ionic liquid of the present invention, i.e. $[Cat^+][X^-]$, is formed in-situ in the composition, by combining: (i) a first ionic liquid having the cation $[Cat^+]$ as defined above and an anion, with (ii) a second ionic liquid having a cation and an anion $[X^-]$ as defined above. The first and second ionic liquids may be used in different amounts, thereby giving a composition in which the cation $[Cat^+]$ and anion $[X^-]$ of the ionic liquid are used in different amounts.

Preferably the cation $[Cat^+]$ of the ionic liquid is present in the composition in a concentration of at least 0.001 M, preferably from 0.005 M to 0.01 M.

Preferably the anion $[X^-]$ of the ionic liquid is present in the composition in a concentration of at least 0.001 M. Whilst the use of a phosphinate anion improves the levels at which the rare earth metals are extracted, it can lead to a decrease in selectivity between different rare earth metals. Thus, in some embodiments, it is preferred for the concentration of phosphinate anion in the composition to be limited, e.g. to a concentration of up to 0.02 M. Preferably, the anion of the ionic liquid is present in the composition in a concentration of from 0.005 M to 0.01 M.

It will be appreciated that the concentration of the ionic liquid in the composition may be varied in order to achieve a particular target viscosity for the composition. It will also be appreciated that the character of the lower viscosity ionic liquid or other diluent may be varied in order to obtain a particular viscosity level.

In preferred embodiments, the viscosity of the composition is in the range of from 50 to 500 mPa·s at 298K, when the composition comprises a solution of the ionic liquid in a lower viscosity ionic liquid. When the ionic liquid is in a solution of an organic solvent, it will be appreciated that the composition will likely have a lower viscosity, for example, less than 50 mPa·s. Viscosity may be measured by any suitable method, for example viscosity may be measured using a rotating disk viscometer with variable temperature.

In some embodiments, the acidic solution is obtainable by leaching the rare earth metal from its source using an acid, for example a mineral acid such as hydrochloric, nitric, perchloric or sulfuric acid, typically hydrochloric or nitric acid. Preferably, the source of the rare earth metal is a mineral or a waste material. However, it will be appreciated that the acidic solution of the rare earth metal or mixture of rare earth metals may be obtained in any suitable way from any rare earth metal source.

The concentration of rare earth metals in the acidic solution is typically from 60 ppm to 2000 ppm. Nonetheless, it will be appreciated that any suitable concentration of rare earth metals in the acid solution may be used.

Typically, rare earth metals are obtained from rare earth ores, which are mined and processed by a variety of methods depending on the particular ore. Such processes are well known in the art. Usually, following mining such processes may include steps such as grinding, roasting to remove carbonates, chemical processing (e.g. alkali/hydroxide treatment), and ultimately leaching with acid to obtain an aqueous acidic solution containing a mixture of rare earth metals.

Examples of rare earth metal bearing minerals contained in rare earth ores are aeschynite, allanite, apatite, bastnssite, brannerite, britholite, eudialyte, euxenite, fergusonite, gadolinite, kainosite, loparite, monazite, parisite, perovskite, pyrochlore, xenotime, yttrocerite, huanghoite, cebaite, florencite, synchysite, samarskite, and knopite.

Rare earth metals may also increasingly be obtained from recycled materials. As global demand for rare earth metals grows, it is increasingly attractive to obtain earth metals from recycled waste materials, particularly in countries with a lack of minable rare earth ore deposits. Rare earth waste materials may be obtained from various sources, for example direct recycling of rare earth scrap/residues from pre-consumer manufacturing, "urban mining" of rare earth containing end of life products, or landfill mining of urban and industrial waste containing rare earths. As rare earth metals are increasingly being used in consumer products, the amount of rare earth metals that can be obtained from such waste materials is also growing.

Waste materials that may contain rare earth metals include, magnetic swarf and rejected magnets, rare earth containing residues from metal production/recycling (e.g. postsmelter and electric arc furnace residues or industrial residues such as phosphogypsum and red mud), phosphors such as those in fluorescent lamps, LEDs, LCD backlights, plasma screens and cathode ray tubes, permanent magnets (e.g. NdFeB) such as those used in automobiles, mobile phones, hard disk drives, computers and peripherals, electronic kitchen utensils, hand held tools, electric shavers, industrial electric motors, electric bicycles, electric vehicle and hybrid vehicle motors, wind turbine generators, nickel-metal hydride batteries such as are used for rechargeable batteries and electric and hybrid vehicle batteries, glass polishing powders, fluid cracking catalysts and optical glass. Major end-of-life waste material sources of rare earths in terms of value are permanent magnets, nickel-metal hydride batteries and lamp phosphors, as well as scrap in the form of magnetic swarf waste.

Rare earth metals will usually be extracted from waste materials by leaching with mineral acids and optionally further processing to remove impurities such as transition metals. This results in an acidic solution of the rare earth metals, which may be used as a source for separation and purification of the individual rare earth metals.

Thus, it is an advantage of the present invention that rare earth metals may be extracted with high selectivity and extractability directly from an acidic solution of the rare earth metal, which may be conveniently obtained from the extraction process of an ore or a waste material.

In a further aspect of the present invention, there is provided an ionic liquid ($[Cat^+][X^-]^-$) substantially as described previously herein.

In a further aspect of the present invention, there is provided a composition substantially as described previously herein.

In some preferred embodiments, the composition further comprises a rare earth metal. It will be appreciated that the composition comprising a rare earth metal may be a valuable resource in itself and it will not always be desirable to separate the rare earth metal, for example by stripping with acid.

For example, the composition further comprising a rare earth metal may be used for electrodeposition of the rare earth metal or precipitation of one or more rare earth metals (e.g. with oxalic acid).

Electrodeposition of rare earth metals from ionic liquids and precipitation of rare earth metals from solution are well known in the art any may be performed in any suitable way, as will be appreciated by one skilled in the art.

In a further aspect of the present invention, there is provided the use of the composition further comprising a rare earth metal for electrodeposition of a rare earth metal.

In a further aspect of the present invention, there is provided the use of the composition further comprising a rare earth metal for precipitation of a rare earth metal.

In a further aspect of the present invention, there is provided a method for preparing an ionic liquid as defined herein, said method comprising reacting:

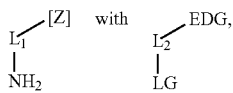

where: LG represents a leaving group, and, where LG is not the same as X, carrying out the following reaction:

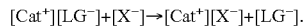

Where LG is the same as X, i.e. the cation is prepared in the form of an anionic liquid having the formula [Cat$^+$][X$^-$], then it is not necessary to carry out an anion exchange reaction. However, where the target ionic liquid has a different anion from that present in [Cat$^+$][LG$^-$], then it is necessary to carry out an anion exchange reaction with anion [X$^-$].

A "leaving group" as used herein will be understood to mean a group that may be displaced from a molecule by reaction with a nucleophilic centre, in particular a leaving group will depart with a pair of electrons in heterolytic bond cleavage. A leaving group is usually one that is able to stabilize the additional electron density that results from bond heterolysis.

Such groups are well-known in the field of chemistry.

It will be understood that the group [Z] may be any group that is able to displace the leaving group to form a [Z$^+$] cation as defined previously herein.

It will be appreciated that a leaving group as defined herein will be such that the primary amine coupled by L$_1$ to [Z] may displace the leaving group to form a bond between the nitrogen and an L$_2$ group, and such that the group [Z] can displace the leaving group to form a bond between [Z] and an L$_2$ group.

Leaving groups may, for example, include a group selected from dinitrogen, dialkyl ethers, perfluoroalkylsulfonates such as triflate, tosylate or mesylate, halogens such as Cl, Br and I, water, alcohols, nitrate, phosphate, thioethers and amines. Preferably, the leaving group LG is selected from halides, more preferably the leaving group LG is Cl.

Such substitution reactions as described herein are well-known in the art and could be performed by a skilled person without difficulty.

By preparing an ionic liquid by this method, an ionic liquid having advantageous rare earth metal extraction properties may be conveniently synthesised in few steps, reducing the increased costs associated with multiple step syntheses.

In a further aspect of the present invention, there is provided the use of the ionic liquid or the composition further comprising a rare earth metal as described herein for extracting rare earth metals. Preferably, the ionic liquid or the composition is used to preferentially extract a first rare earth metal from a solution which comprises a first and a second rare earth metal.

The present invention will now be illustrated by way of the following examples and with reference to the following figures in which.

EXAMPLES

Example 1: Synthesis of Ionic Liquid

Figure 1:
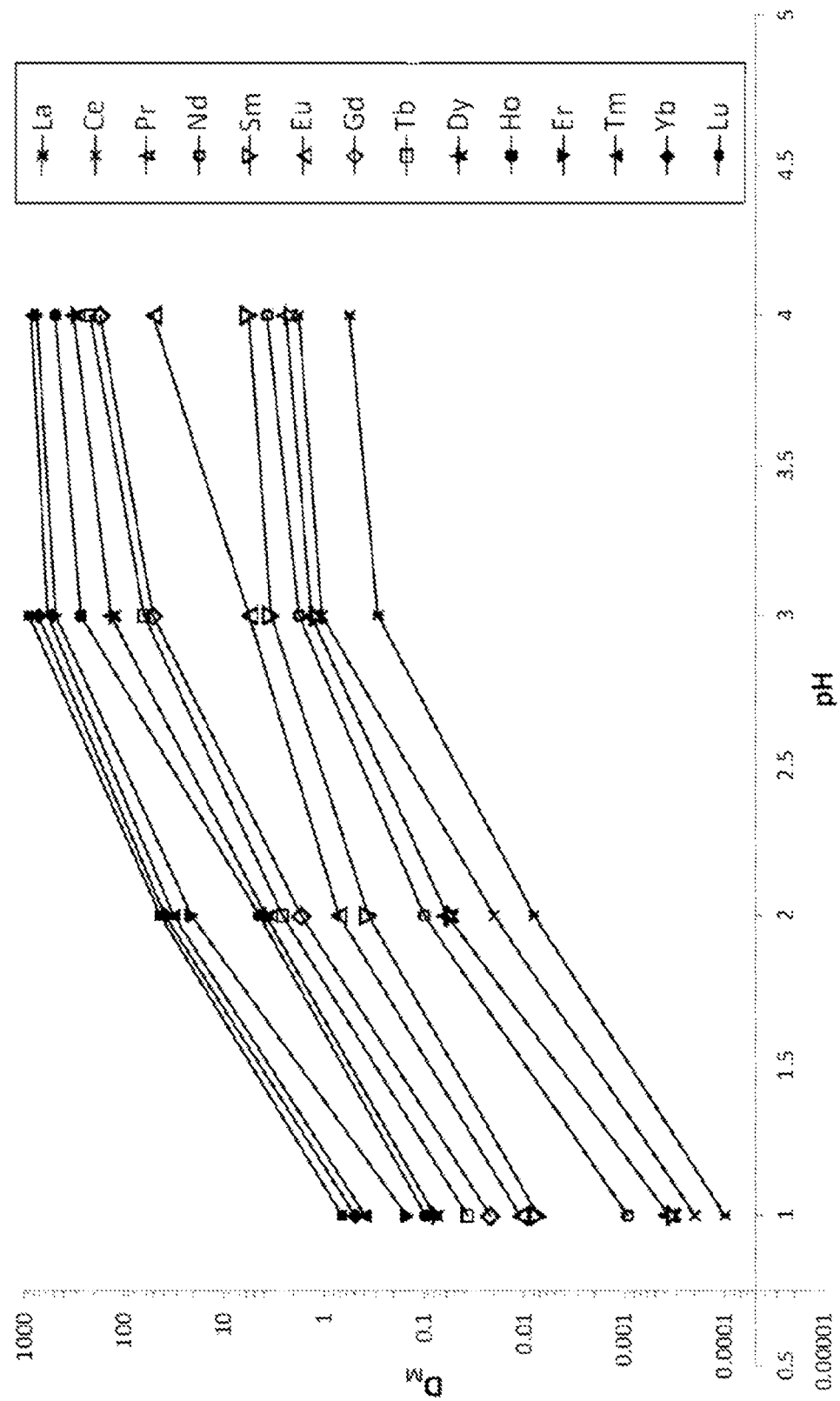
FIG. 1 is a graph showing the distribution factors for the extraction of a selection of rare earth metals according to an embodiment of the present invention.
Figure 2:
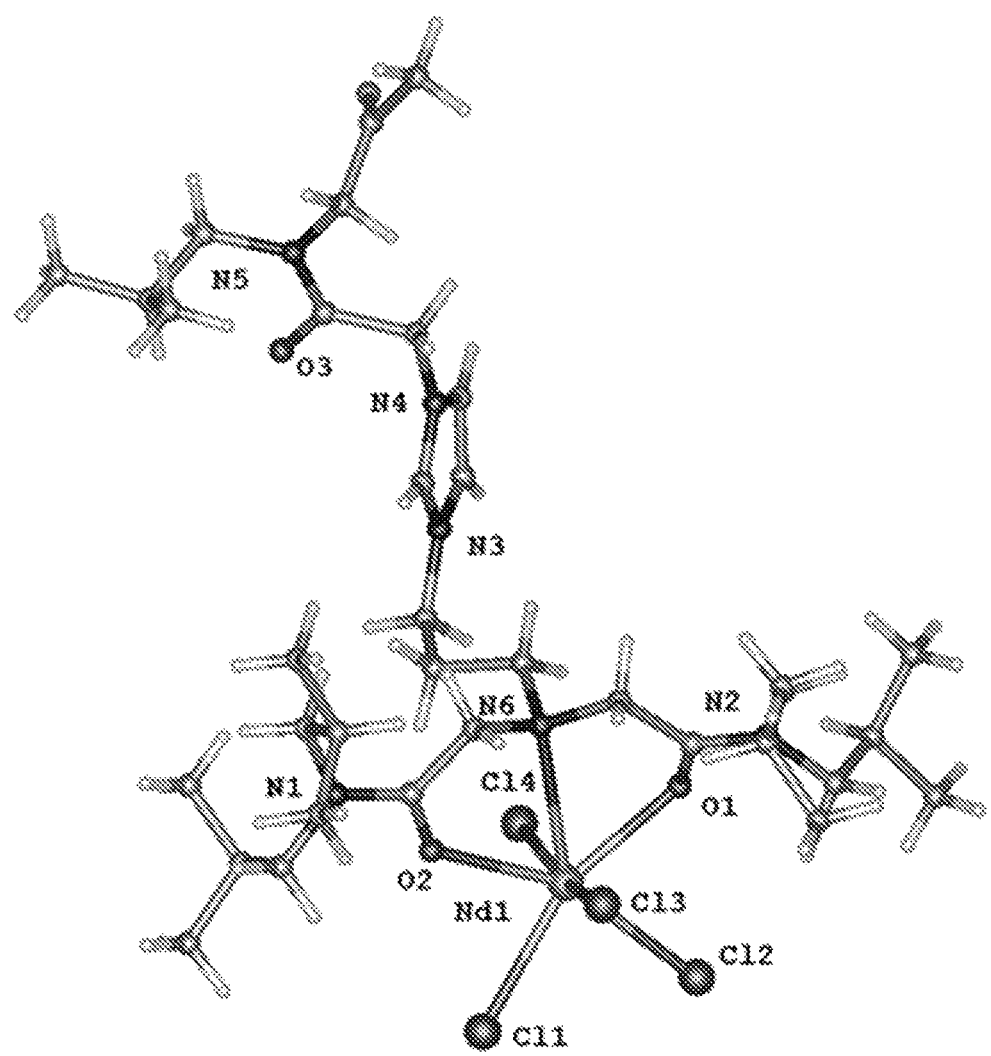
FIG. 2 shows the crystal structure of the [MAIL]$^+$ cation coordinating to Nd after extraction from an acidic (HCl) solution containing NdCl$_3$.6H$_2$O.

General procedure for the synthesis of an ionic liquid according to embodiments of the invention A reaction mixture comprising 3 moles of an N,N-dialkyl-2-chloroacetamide and a substrate having the structure H$_2$N-L$_1$-[Z] were stirred in a halogenated solvent (e.g. CHCl$_3$, CH$_2$Cl$_2$, etc.) or an aromatic solvent (e.g. toluene, xylene, etc.) at 60 to 70° C. for 7 to 15 days. After cooling, the solid was filtered off and the organic phase was repeatedly washed with 0.1 to 0.2 M HCl until the aqueous phase showed milder acidity (pH 2). The organic phase was then washed with 0.1 M Na$_2$CO$_3$ (2-3 washes) and finally was washed with deionized water until the aqueous phase showed a neutral pH. The solvent was removed under high vacuum to give an ionic liquid product (with a chloride anion) as a highly viscous liquid. The chloride anion could be exchanged for a phosphinate anion (e.g. bis(2,4,4-trimethylpenthyl)phosphinate) using conventional metathesis routes to give the ionic liquid of the present invention. For example, anion exchange could be achieved by reacting with an alkali metal salt of the phosphinate anion with the ionic liquid in an organic solvent, or by combining the chloride anion ionic liquid product with a further ionic liquid having a phosphinate anion.

Synthesis of an Imidazolium Ionic Liquid

[MAIL$^+$][NTf$_2^-$]:

Synthesis of an imidazolium ionic liquid

[MAIL$^+$][NTf$_2^-$]:

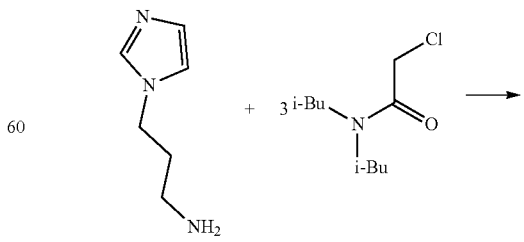

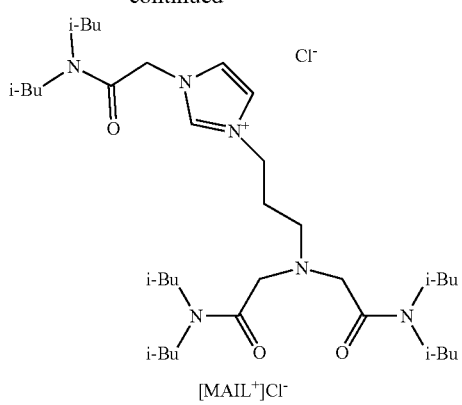

[MAIL+]Cl−

1-(3-Aminopropyl)-imidazole (0.05 mol) was added to of N,N-diisobutyl-2-chloroacetamide (0.15 mol) in a 500 ml three necked round bottom flask. Triethylamine (0.11 moles) was then added along with chloroform (200 ml). The reaction was stirred for 6 hours at room temperature and then stirred at 60 to 70° C. for 7 days. The reaction mixture was then cooled and after filtration it was successively washed with 0.1 M HCl, 0.1 M Na$_2$CO$_3$ and deionized water (as described in general procedure). The solvent was removed from the neutralised organic phase at 8 mbar (6 mm Hg) and finally at 60° C. and 0.067 mbar (0.05 mmHg). The ionic liquid [MAIL+]Cl− was recovered as a highly viscous yellow liquid.

Ionic liquid [MAIL+]Cl− (0.025 mol) was dissolved in chloroform and lithium bis-(trifluoromethane) sulfonamide (LiNTf$_2$) (0.03 mol) was added. The reaction mixture was stirred for 1 hour and then the organic phase was repeatedly washed with deionized water. Finally the solvent was removed from the organic phase under vacuum (0.13 mbar, 0.1 mm Hg) at 65° C. to yield the bistriflimide anion ionic liquid [MAIL+][NTf$_2$−].

[MAIL-6C+][NTf$_2$−]:

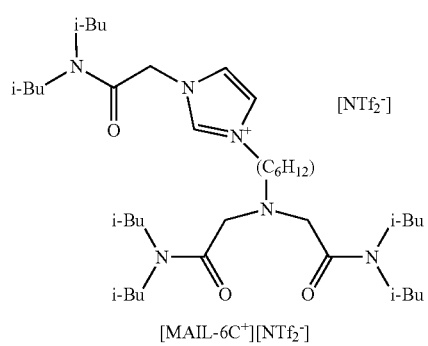

[MAIL-6C+][NTf$_2$−]

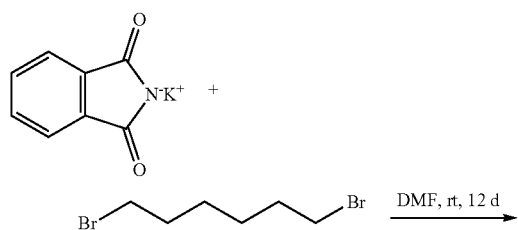

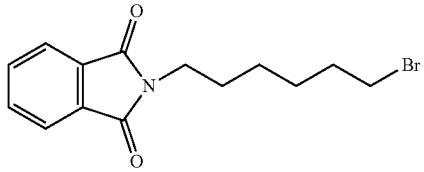

3

A mixture of potassium pthalimide (10.0 g, 54.0 mmol) and 1,6-dibromobutane (9.97 mL, 64.8 mmol) in dry DMF (100 mL) was stirred at room temperature for 12 days. The mixture was concentrated and extracted with chloroform (3×30 mL) and washed with deionised water (3×80 mL) and brine (100 mL). The organic layer was dried over magnesium sulfate and concentrated to give a white syrup. The syrup was triturated with hexanes, filtered and dried to give a white solid product (3) (14.3 g, 85%).

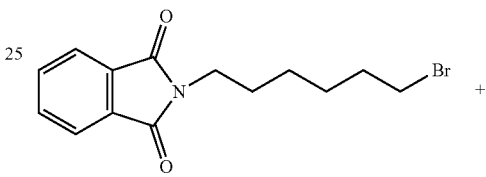

3

NaH, THF, reflux
overnight

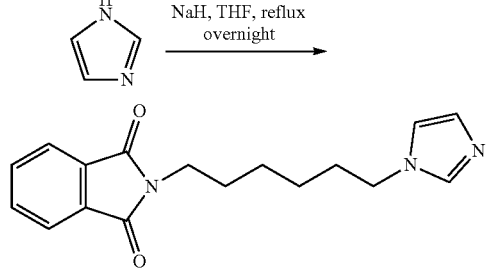

4

To NaH (0.645 g, 26.9 mmol) in THF was added at 0° C. under N$_2$, imidazole (1.21 g, 17.7 mmol) in THF was added over 30 mins, and stirred for a further 30 mins at 0° C. 3 (5.00 g. 16.1 mmol) in THF was added at 0° C. and the mixture stirred for 1 hour at room temperature, then refluxed at 70° C. overnight. The mixture was filtered and the residual NaBr was washed with THF. The filtrate was concentrated to give a syrup which was dissolved in DCM to give a yellow solution which was then washed with water and dried over sodium sulfate and triturated with hexanes to precipitate a white solid which was filtered and washed with hexanes (4) (1.52 g, 32%).

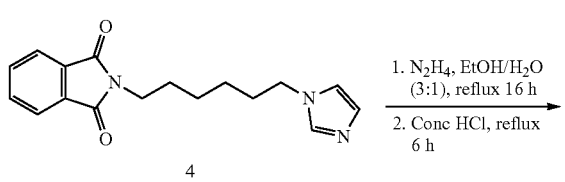

4

1. N$_2$H$_4$, EtOH/H$_2$O (3:1), reflux 16 h
2. Conc HCl, reflux 6 h

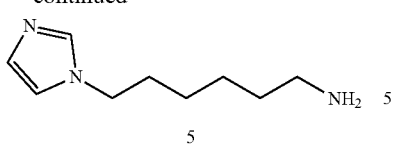

5

4 (0.750 g, 2.54 mmol) was dissolved in a EtOH:H₂O mixture (160 mL, 3:1) and hydrazine hydrate (50-60%, 0.174 mL, 5.55 mmol) was added at room temperature and the mixture refluxed overnight. The solution was cooled to room temperature and concentrated HCl (2 mL) was added, the reaction mixture changed from colourless to yellow to red to light yellow during the addition. The mixture was stirred at reflux for 6 hours and filtered. The solution was concentrated and dissolved in distilled water to give a yellow solution. Sodium hydroxide was added until the mixture reached pH 11, it was then extracted with chloroform (4×40 mL), dried over magnesium sulfate and concentrated to give an orange oil (5) (0.329 g, 78%).

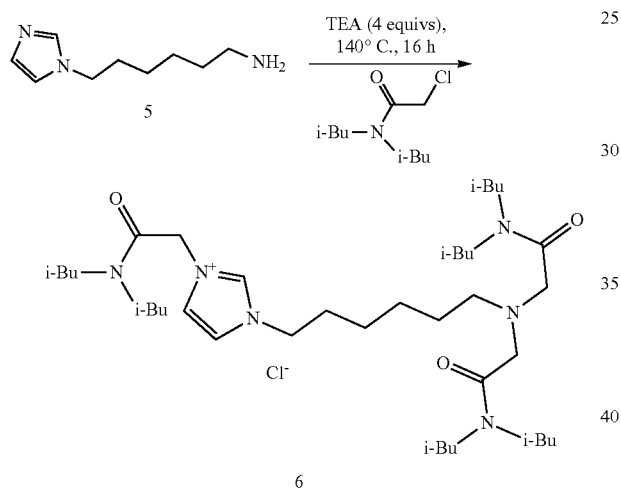

6

To a high pressure vessel was added 5 (0.257 g, 1.54 mmol), triethylamine (0.623 g, 6.16 mmol), N,N-diisobutyl-2-chloroacetamide (0.950 g, 4.62 mmol) and chloroform (5 mL). The vessel was stoppered and stirred at 140° C. on an oil bath for 16 hours. The reaction mixture was washed with pH 1 HCl (40 mL), Na₂CO₃ (2×40 mL) then water (4×40 mL). The organic layer was dried over magnesium sulfate and concentrated in vacuo to give a viscous dark brown liquid (6) (0.648 g, 59%).

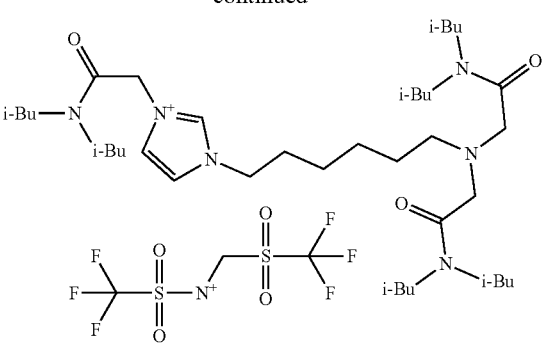

To a round bottom flask was added 6 (0.6255 g, 0.88 mmol) followed by DCM (50 mL). LiNTf₂ (0.7572 g, 2.64 mmol) was added followed by water (50 mL). The reaction mixture was stirred at room temperature for 24 hours. The aqueous layer was removed and the organic layer washed with deionised water (4×40 mL). The organic layer was dried over magnesium sulfate and concentrated. The product was dried overnight to give a black viscous liquid, [MAIL-6C⁺][NTf₂⁻], (0.7467 g, 89%).

[MAIL-Ph⁺][NTf₂⁻]:

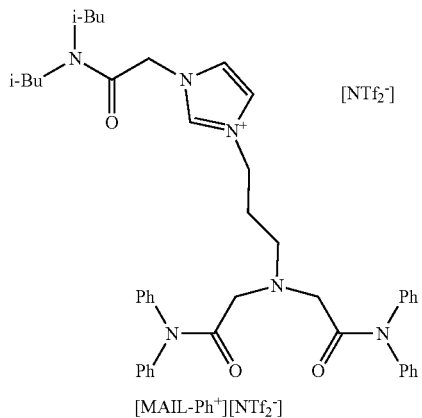

[MAIL-Ph⁺][NTf₂⁻]

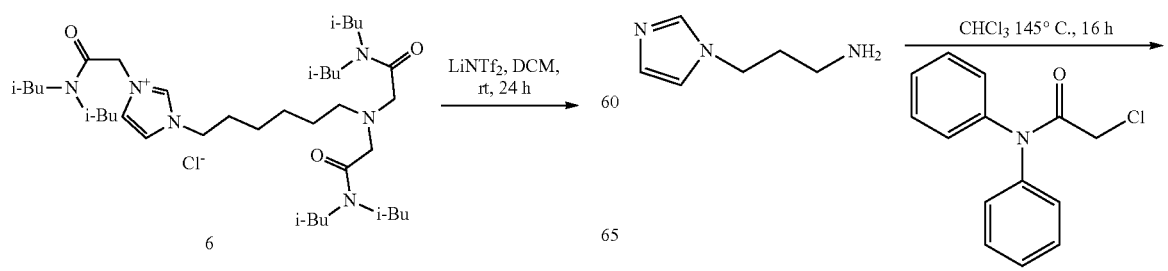

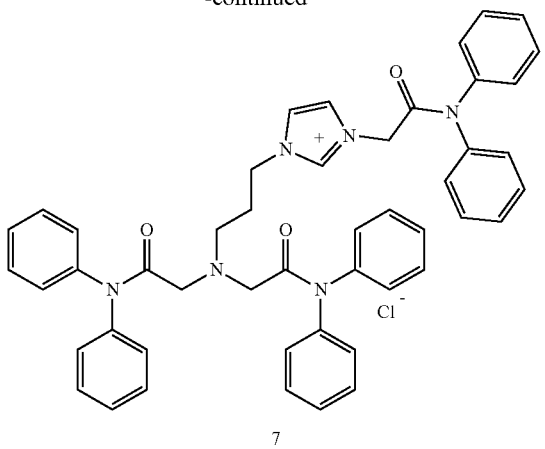

To a high pressure vessel was added 1-(3-aminopropyl) imidazole (0.200 g, 1.60 mmol), triethylamine (0.647 g, 6.39 mmol), 2-chloro-N,N-diphenylacetamide (1.18 g, 4.49 mmol) and chloroform (5 mL). The vessel was stoppered and stirred at 145° C. on an oil bath for 16 hours. The reaction mixture was washed with pH 1 HCl (15 mL), then water (4×150 mL). The organic layer was dried over magnesium sulfate and concentrated in vacuo to give an orange/brown solid (7) (0.883 g, 70%).

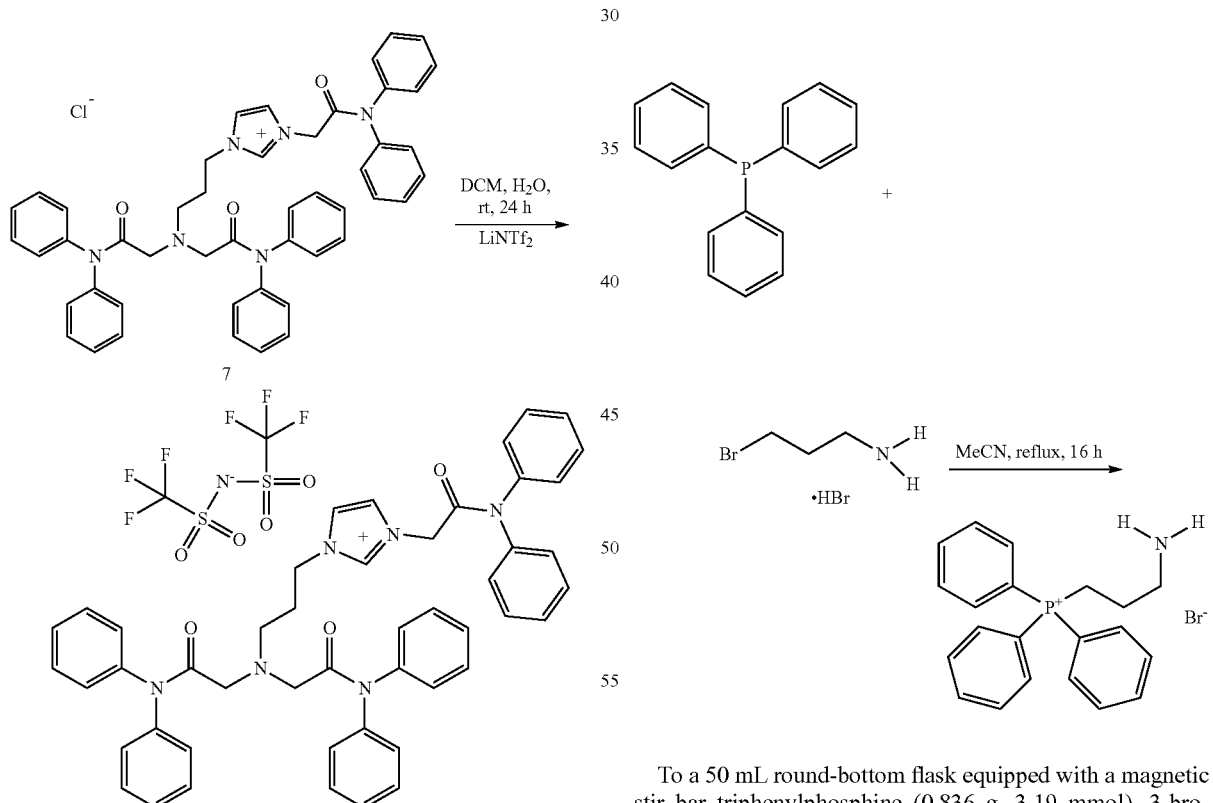

To a 50 mL round-bottom flask was added 7 (0.444 g, 0.560 mmol) followed by DCM (20 mL). LiNTf$_2$ (0.484 g, 1.69 mmol) was added followed by deionised water (20 mL). The reaction mixture was stirred at room temperature for 24 hours. The aqueous layer was removed and the organic layer washed with deionised water (5×15 mL). The organic layer was dried over magnesium sulfate and concentrated. The product was dried overnight to give a viscous brown liquid, [MAIL-Ph$^+$][NTf$_2^-$], (0.351 g, 65%).

The bistriflimide anion ionic liquid ([MAIL$^+$][NTf$_2^-$]$^-$) was added to the ionic liquids [P$_{666(14)}^+$][NTf$_2^-$] and [P$_{666(14)}^+$][R$_2$P(O)O$^-$], where R=2,4,4-trimethylpentyl, to form an extraction composition in situ comprising an ionic liquid of the present invention ([MAIL$^+$][R$_2$P(O)O$^-$]$^-$).

The phosphinate ionic liquid [MAIL$^+$][R$_2$P(O)O$^-$] (R=2,4,4-trimethylpentyl) was also synthesised by ion exchange.

Synthesis of phosphonium ionic liquids

[MAIL-PPh$_3^+$][NTf$_2^-$]:

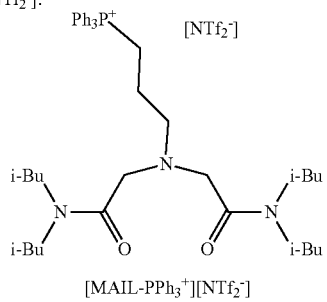

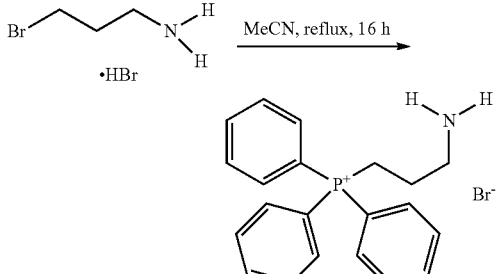

To a 50 mL round-bottom flask equipped with a magnetic stir bar triphenylphosphine (0.836 g, 3.19 mmol), 3-bromopropylamine hydrobromide (1.00 g, 4.57 mmol), and acetonitrile (25 mL) were added. The suspension was then heated and stirred at reflux for 16 hours. The reaction was cooled to room temperature, and the solvent was removed under reduced pressure, and the resulting white solid was then dried in vacuo, and used in subsequent steps without further purification (1.01 g, 79%).

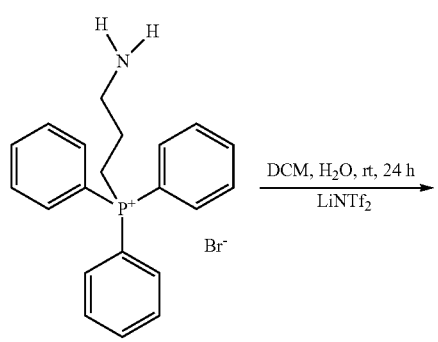

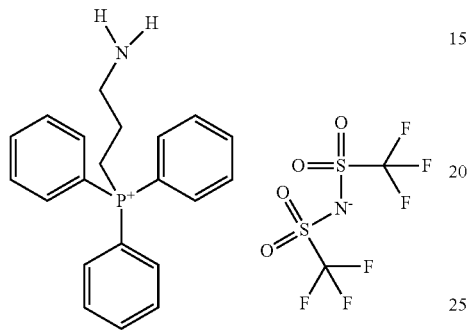

To a 50 mL round-bottom flask was added (3-Aminopropyl)(triphenyl)phosphonium bromide (1.01 g, 0.252 mmol) followed by DCM (20 mL). LiNTf$_2$ (2.17 g, 7.55 mmol) was added followed by deionised water 20 mL). The reaction mixture was stirred at room temperature for 24 hours. The aqueous layer was removed and the organic layer washed with deionised water (5×15 mL). The organic layer was dried over magnesium sulfate and concentrated. The product was dried overnight to give a white solid (1.26 g, 84%).

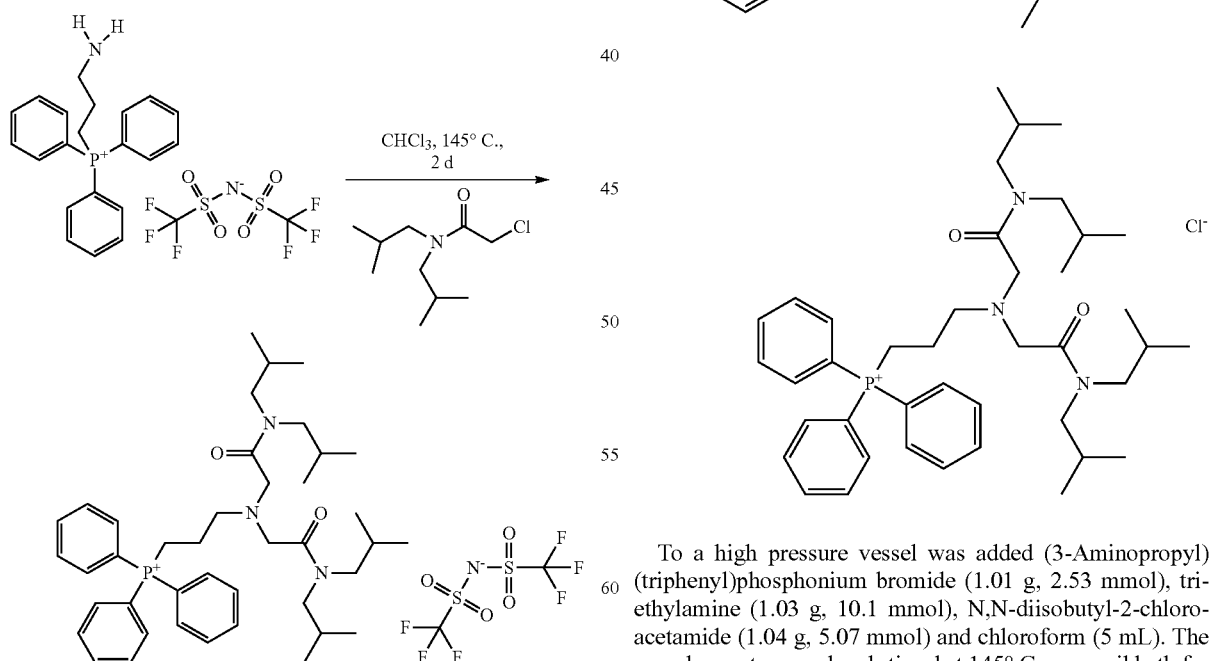

To a high pressure vessel was added (3-Aminopropyl)(triphenyl)phosphonium bistriflimide (0.200 g, 0.333 mmol), triethylamine (0.135 g, 1.33 mmol), N,N-diisobutyl-2-chloroacetamide (0.137 g, 0.666 mmol) and chloroform (5 mL). The vessel was stoppered and stirred at 145° C. on an oil bath for 48 hours. The reaction mixture was washed with pH 1 HCl (15 mL), then water (4×150 mL). The organic layer was dried over magnesium sulfate and concentrated in vacuo to give a viscous dark brown liquid, [MAIL-PPh$_3^+$][NTf$_2^-$], (0.282 g, 90%).

[MAIL-PPh$_3^+$][R$_2$P(O)O$^-$]:

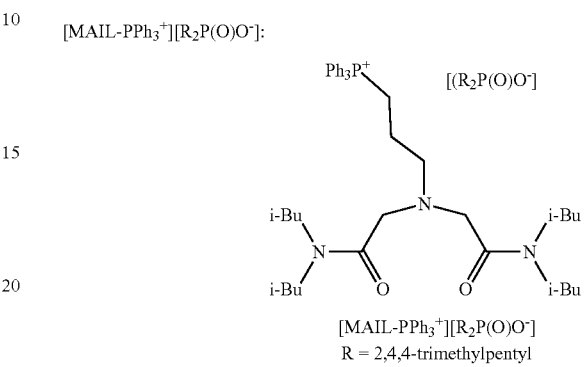

[MAIL-PPh$_3^+$][R$_2$P(O)O$^-$]
R = 2,4,4-trimethylpentyl

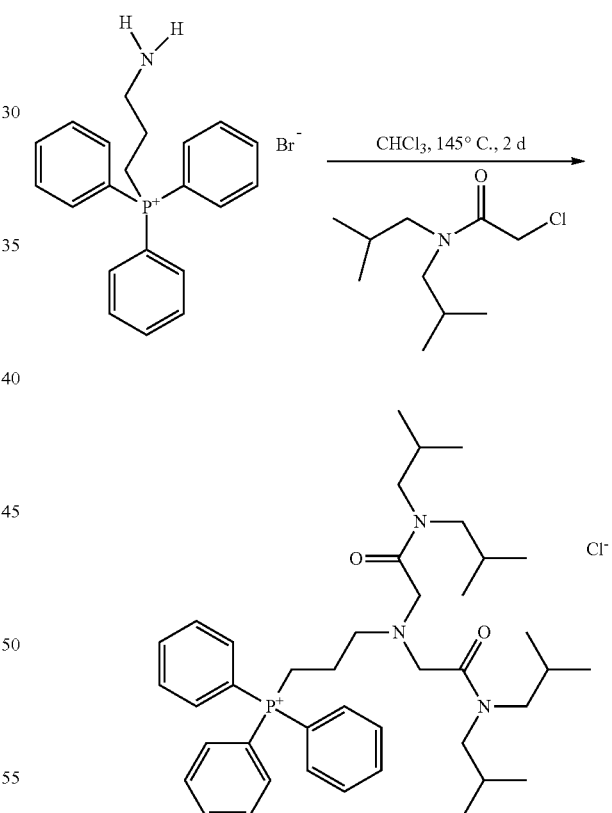

To a high pressure vessel was added (3-Aminopropyl)(triphenyl)phosphonium bromide (1.01 g, 2.53 mmol), triethylamine (1.03 g, 10.1 mmol), N,N-diisobutyl-2-chloroacetamide (1.04 g, 5.07 mmol) and chloroform (5 mL). The vessel was stoppered and stirred at 145° C. on an oil bath for 48 hours. The reaction mixture was washed with pH 1 HCl (15 mL), then water (4×150 mL). The organic layer was dried over magnesium sulfate and concentrated in vacuo to give a viscous dark brown liquid (0.981 g, 56%).

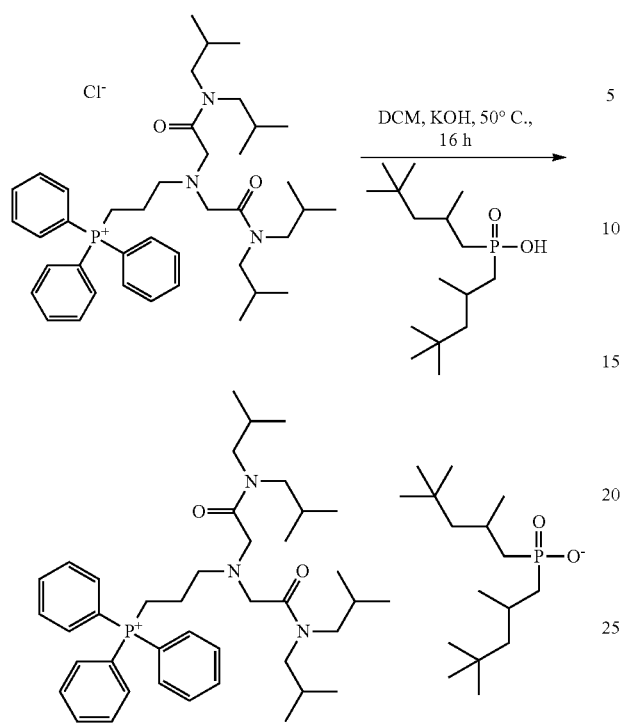

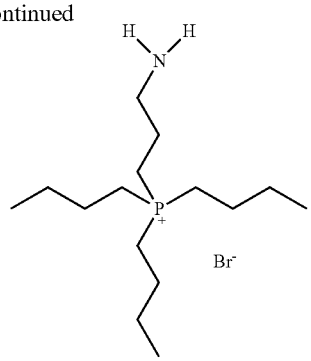

To a 50 mL round-bottom flask was added the phosphonium diamide (0.898 g, 1.29 mmol) followed by DCM (20 mL). $R_2P(O)OH$ (R=2,4,4-trimethyl pentyl) (0.356 g, 1.29 mmol) was added followed by a KOH solution (40%, 20 mL). The reaction mixture was stirred at 50° C. for 16 hours. The aqueous layer was removed and the organic layer washed with deionised water (5×15 mL). The organic layer was dried over magnesium sulfate and concentrated. The product was dried overnight to give a white solid, [MAIL-PPh$_3^+$][R$_2$P(O)O$^-$], (0.943 g, 77

To a 50 mL round-bottom flask equipped with a magnetic stir bar tributylphosphine (0.823 g, 4.07 mmol), 3-bromopropylamine hydrobromide (0.890 g, 4.07 mmol), and acetonitrile (25 mL) were added. The suspension was then heated and stirred at reflux for 48 hours. The reaction was cooled to room temperature, and the solvent was removed under reduced pressure, and the resulting oil was then dried in vacuo, and used in subsequent steps without further purification (1.24 g, 89%).

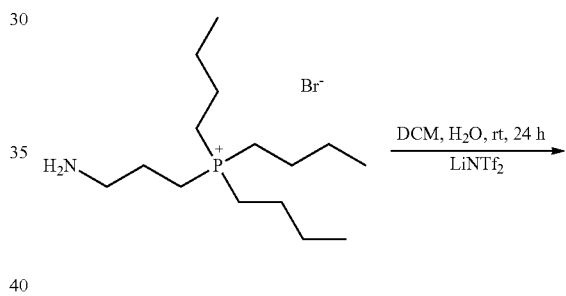

[MAIL-P$_{444}^+$][NTf$_2^-$]:

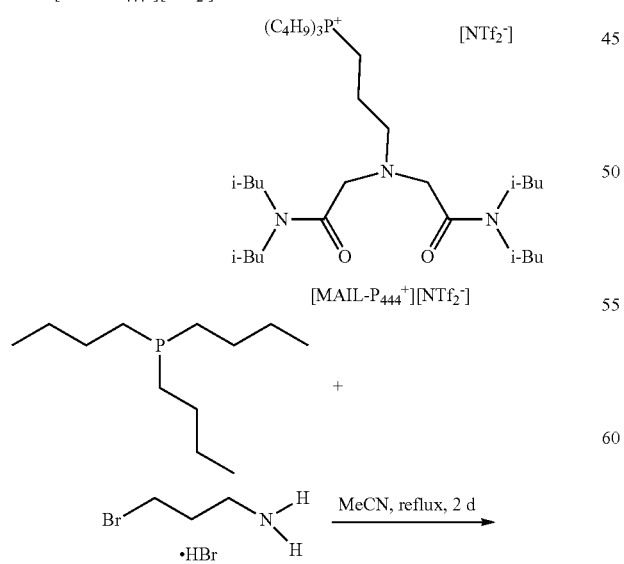

To a 50 mL round-bottom flask was added (3-Aminopropyl)(tributyl)phosphonium bromide (0.559 g, 1.64 mmol) followed by DCM (20 mL). LiNTf$_2$ (1.41 g, 4.93 mmol) was added followed by deionised water (20 mL). The reaction mixture was stirred at room temperature for 24 hours. The aqueous layer was removed and the organic layer washed with deionised water (5×15 mL). The organic layer was dried over magnesium sulfate and concentrated. The product was dried overnight to give a colourless oil (0.304 g, 34%).

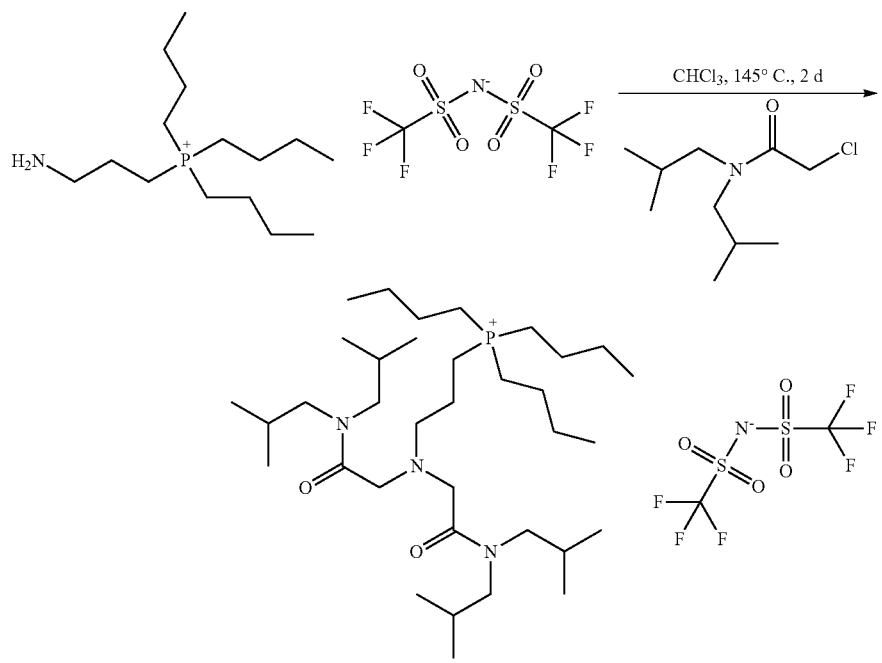

To a high pressure vessel was added (3-Aminopropyl)(tributyl)phosphonium bistriflimide (0.200 g, 0.370 mmol), triethylamine (0.150 g, 1.48 mmol), N,N-diisobutyl-2-chloroacetamide (0.152 g, 0.740 mmol) and chloroform (5 mL). The vessel was stoppered and stirred at 145° C. on an oil bath for 48 hours. The reaction mixture was washed with pH 1 HCl (15 mL), then water (4×150 mL). The organic layer was dried over magnesium sulfate and concentrated in vacuo to give a viscous dark brown liquid, [MAIL-P$_{444}$+][NTf$_2$−], (0.250 g, 77%).

[MAIL-P$_{888}$+][NTf$_2$−]:

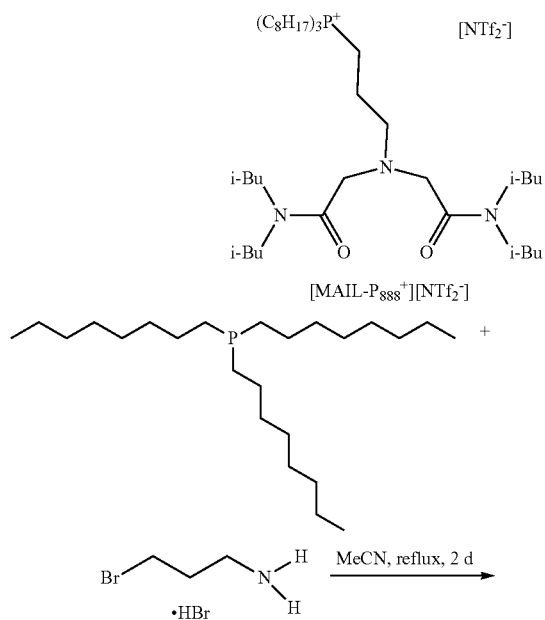

-continued

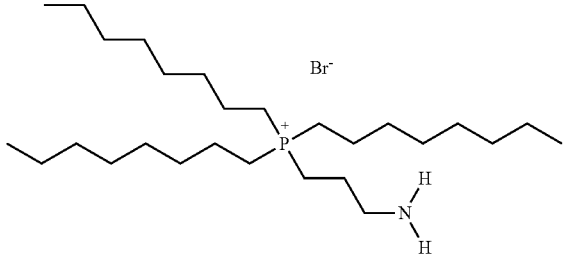

To a 50 mL round-bottom flask equipped with a magnetic stir bar trioctylphosphine (0.872 g, 2.35 mmol), 3-bromopropylamine hydrobromide (0.500 g, 2.28 mmol), and acetonitrile (25 mL) were added. The suspension was then heated and stirred at reflux for 48 hours. The reaction was cooled to room temperature, and the solvent was removed under reduced pressure, and the resulting oil was then dried in vacuo, and used in subsequent steps without further purification (0.889 g, 85%).

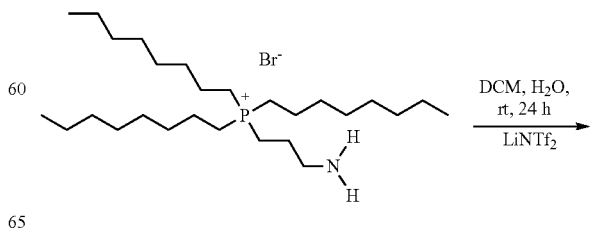

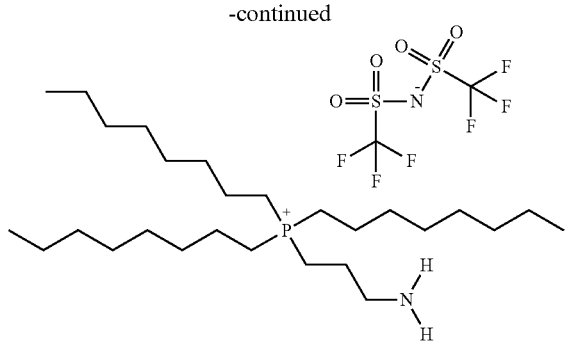

To a 50 mL round-bottom flask was added (3-Aminopropyl)(trioctyl)phosphonium bromide (0.564 g, 1.11 mmol) followed by DCM (20 mL). LiNTf$_2$ (0.954 g, 3.32 mmol) was added followed by deionised water (20 mL). The reaction mixture was stirred at room temperature for 24 hours. The aqueous layer was removed and the organic layer washed with deionised water (5×15 mL). The organic layer was dried over magnesium sulfate and concentrated.

The product was dried overnight to give a colourless oil (0.542 g, 69%).

was dried over magnesium sulfate and concentrated in vacuo to give a viscous dark brown liquid, [MAIL-P$_{888}$$^+$][NTf$_2$$^-$], (0.313 g, 99

Example 2: Liquid-Liquid Extraction of Rare Earth Metals Using [MAIL$^+$][NTf$_2$]

General Procedure for Extraction of Rare Earth Metals

Equal volumes (2 to 5 ml) of the ionic liquid extractant ([MAIL$^+$][NTf$_2$$^-$] in [P$_{666(14)}$$^+$][NTf$_2$$^-$]) and an acidic aqueous feed solution containing rare earth metals in HCl were equilibrated for 15-30 minutes on a wrist action shaker. The phases were centrifuged and the aqueous phase was analysed for rare earth metal content using Inductively Coupled Plasma Optical Emission Spectroscopy (ICP-OES), though it will be appreciated that any suitable analysis technique may be used. The proportion of the rare earth metals extracted into the ionic liquid (organic) phase was determined through mass balance using the ICP-OES measurement.

The distribution ratio of an individual rare earth metal was determined as the ratio of its concentration in the ionic liquid phase to that of it in the aqueous phase (raffinate). $D_M = [M]_{IL}/[M]_{Aq}$, where IL represents ionic liquid phase and Aq represents the aqueous phase (raffinate).

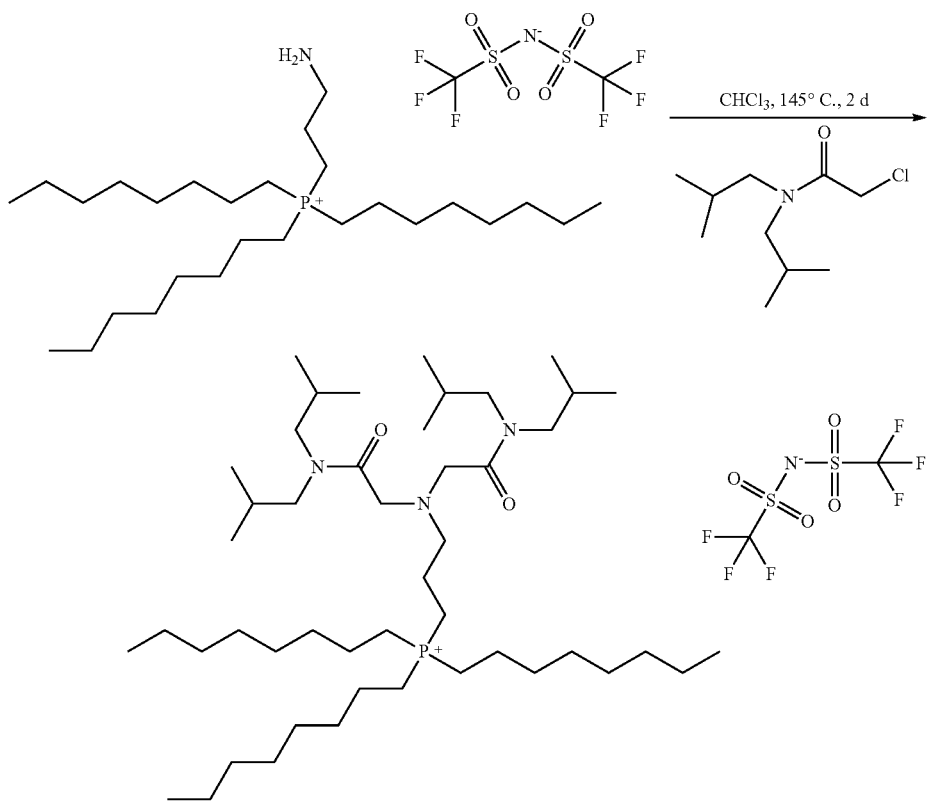

To a high pressure vessel was added (3-Aminopropyl)(trioctyl)phosphonium bistriflimide (0.200 g, 0.282 mmol), triethylamine (0.114 g, 1.13 mmol), N,N-diisobutyl-2-chloroacetamide (0.116 g, 0.564 mmol) and chloroform (5 mL). The vessel was stoppered and stirred at 145° C. on an oil bath for 48 hours. The reaction mixture was washed with pH 1 HCl (15 mL), then water (4×150 mL). The organic layer The separation factor (SF) with respect to an individual rare earth metal pair is expressed as the ratio of the distribution ratio of a first rare earth metal with the distribution ratio of a second rare earth metal. For example, the separation factor of dysprosium with respect to neodymium=$D_{Dy}/D_{Nd}$. It will be appreciated that separation factors estimated from independently obtained distribution ratios will be lower than the actual separation factors, obtained during the separation of mixtures of rare earth metals during a competitive separation (as exemplified below).

Distribution ratios for individual rare earth metals were obtained in separate extractions according to the general procedure above, using 0.0075 M [MAIL$^+$][NTf$_2^-$] in [P$_{666(14)}{}^+$][NTf$_2^-$] and a 200 mg/l (ppm) HCl solution of the relevant rare earth metal chloride (where 200 ppm refers to the concentration of the elemental metal in the solution). FIG. 1 shows a plot of the distribution ratios for each rare earth metal as a function of pH, showing that the ionic liquid according to the present invention may be used to extract rare earth metals across a range of pH values.

Figure 3:
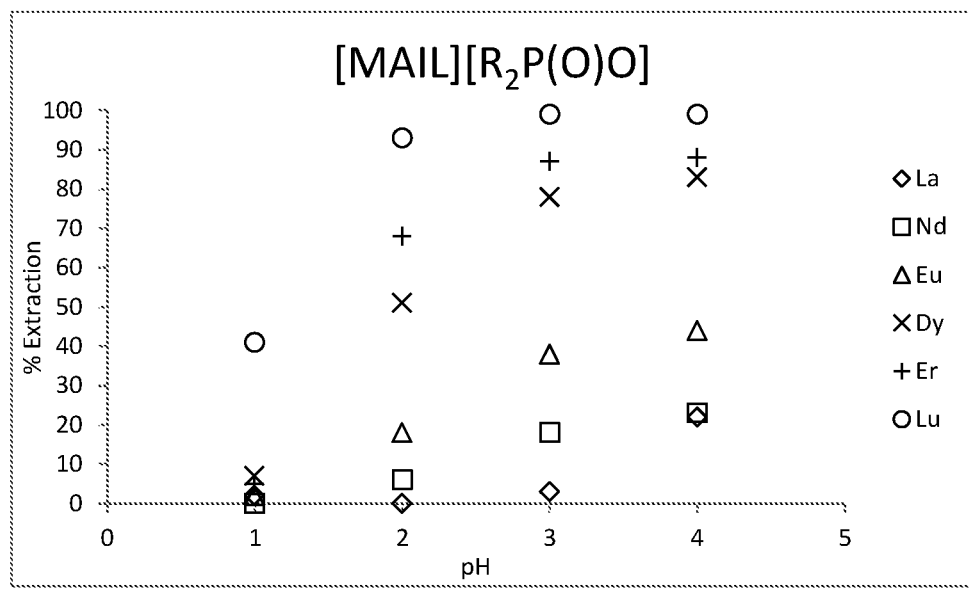
FIG. 3 is a graph showing extraction of a selection of rare earth metals using [MAIL$^+$][R$_2$P(O)O$^-$].
Figure 4:
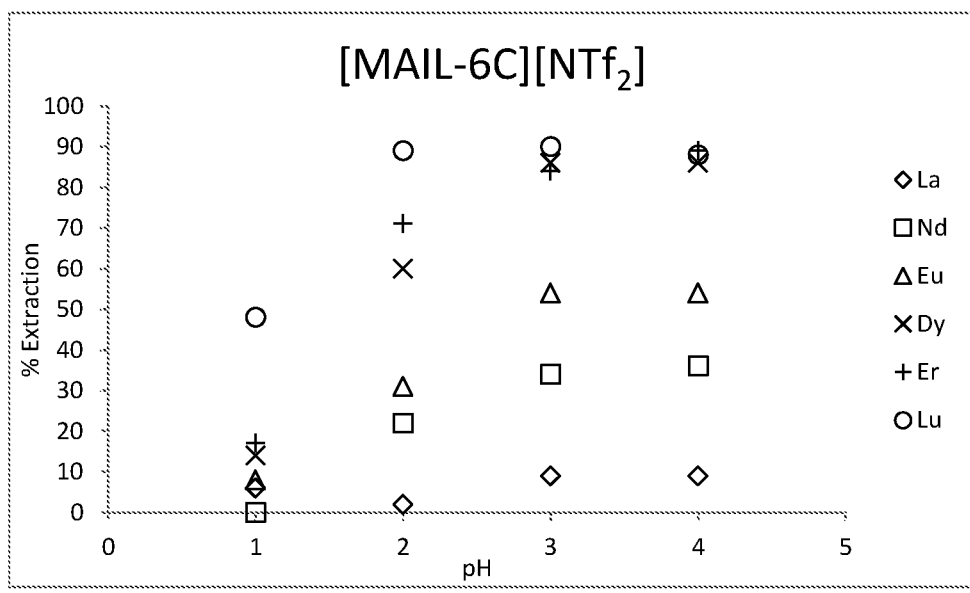
FIG. 4 is a graph showing extraction of a selection of rare earth metals using [MAIL-6C$^+$][NTf$_2^-$].
Figure 5:
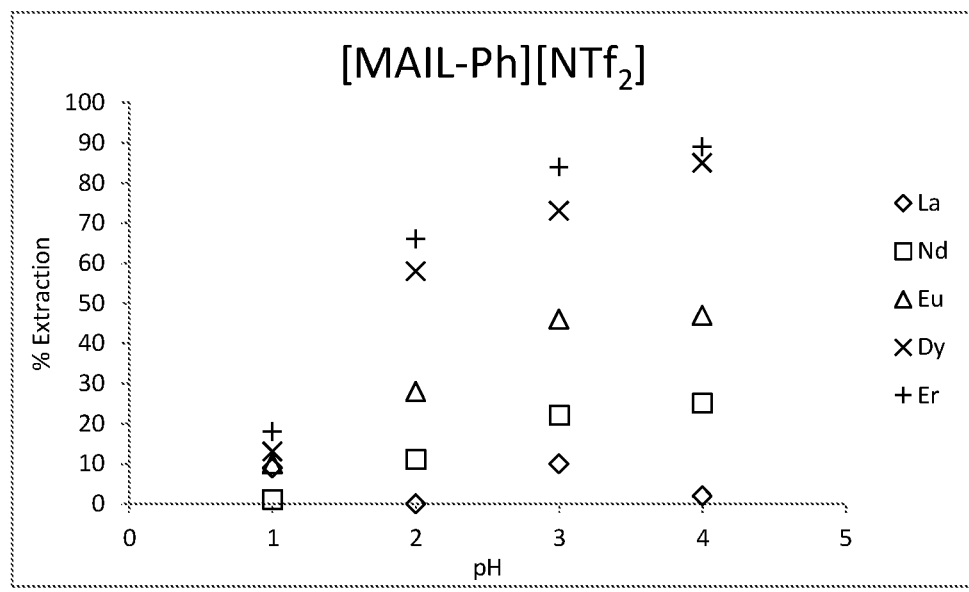
FIG. 5 is a graph showing extraction of a selection of rare earth metals using [MAIL-Ph$^+$][NTf$_2^-$].

The separation of rare earth metals was also performed by the above method using 0.0075 M of the ionic liquids [MAIL$^+$][R$_2$P(O)O$^-$], [MAIL-6C$^+$][NTf$_2^-$] and [MAIL-Ph$^+$][NTf$_2^-$] in [P$_{666(14)}{}^+$][NTf$_2^-$]. These ionic liquids were also found to differentially extract rare earth metals at pH 1 to pH4 as shown in FIGS. 3, 4 and 5.

Recycling of Ionic Liquid

Dy was extracted from an aqueous solution of Dy (180 ppm) at pH4 using 0.025 M [MAIL$^+$][NTf$_2^-$] in [P$_{666(14)}{}^+$][NTf$_2^-$] (>95% extracted) and the ionic liquid stripped at pH 1 using HCl (1:1 ionic liquid to stripping solution ratio) in 4 contacts. The ionic liquid was washed with deionised water to raise the pH to 7, and was used in further extractions. The amount of Dy extracted dropped by around 20% compared to the first extraction, but remained at a constant level over four subsequent extractions.

Separation of Dy and Nd

An aqueous HCl solution containing DyCl$_3$.6H$_2$O (60 mg/l (ppm) Dy) and NdCl$_3$.6H$_2$O (1400 mg/l (ppm) Nd) at pH 3 was extracted with the ionic liquid extractant (0.005 M [MAIL$^+$][NTf$_2^-$] in [P$_{666(14)}{}^+$][NTf$_2^-$]) according to the general procedure above. A single contact (extraction) gave $D_{Dy}$=13.45, $D_{Nd}$=0.0124, giving a SF$_{Dy-Nd}$ of 1085.

This separation factor (1085) is considerably higher than the separation factors obtained for Dy/Nd separation by the systems in the prior art shown in Table 1 (maximum 239).

The above separation was repeated using 0.0075M of an ionic liquid in [P$_{666(14)}{}^+$][NTf$_2^-$] at pH2. The extraction was performed using [MAIL$^+$][NTf$_2^-$], [MAIL$^+$][R$_2$P(O)O$^-$], [MAIL-6C$^+$][NTf$_2^-$], [MAIL-P$_{444}{}^+$][NTf$_2^-$], [MAIL-P$_{888}{}^+$][NTf$_2^-$], [MAIL-PPh$_3+$][NTf$_2^-$] and [MAIL-PPh$_3{}^+$][R$_2$P(O)O$^-$] and the results are shown in Table 2. As can be seen, ionic liquids described herein can be used to completely selectively extract Dy from Nd. Improved extraction and selectivity is also observed in the case of the ionic liquids having a phosphinate anion. Completely selective extraction of Dy from Nd using [MAIL$^+$][NTf$_2^-$], [MAIL$^+$][R$_2$P(O)O$^-$] and [MAIL-6C$^+$][NTf$_2^-$] was also observed at pH 1.8, with extraction of more than 50% Dy.

TABLE 2

| Ionic liquid | Dy % Extraction | Nd % Extraction |
|---|---|---|
| [MAIL$^+$][NTf$_2^-$] | 82 | 0 |
| [MAIL$^+$][R$_2$P(O)O$^-$] | 86.5 | 0 |
| [MAIL-6C$^+$][NTf$_2^-$] | 83 | 0 |
| [MAIL-P$_{444}{}^+$][NTf$_2^-$] | 89 | 0 |
| [MAIL-P$_{888}{}^+$][NTf$_2^-$] | 87 | 0 |
| [MAIL-PPh$_3{}^+$][NTf$_2^-$] | 90 | 0.6 |
| [MAIL-PPh$_3{}^+$][R$_2$P(O)O$^-$] | 90 | 0 |

Separation of Eu and La

An aqueous HCl solution containing EuCl$_3$·6H$_2$O (65 mg/l (ppm) Eu) and LaCl$_3$·7H$_2$O (470 mg/l (ppm) La) at pH 3 was extracted with the ionic liquid extractant (0.005 M [MAIL$^+$][NTf$_2^-$] in [P$_{666(14)}{}^+$][NTf$_2^-$]) according to the general procedure above. A single contact (extraction) gave $D_{Eu}$=9.3, $D_{La}$=0.044, giving a SF$_{Eu-La}$ of 211.

Separation of Tb and Ce

An aqueous HCl solution containing TbCl$_3$.6H$_2$O (530 mg/l (ppm) Tb) and CeCl$_3$.6H$_2$O (950 mg/l (ppm) Ce) at pH 3 was extracted with the ionic liquid extractant (0.0075 M [MAIL$^+$][NTf$_2^-$] in [P$_{666(14)}{}^+$][NTf$_2^-$]) according to the general procedure above. A single contact (extraction) gave $D_{Tb}$=11.2, $D_{Ce}$=0.068, giving a SF$_{Tb-Ce}$ of 162.

Example 3: Stripping of Rare Earth Metals from [MAIL$^+$][NTf$_2^-$]

Dy(III) (80 ppm) was stripped from an organic phase at pH 0.25 comprising [MAIL$^+$][NTf$_2^-$] in [P$_{666(14)}{}^+$][NTf$_2^-$] (0.0075 M) in 3 successive contacts. The organic phase was contacted with an equal volume of an aqueous HCl solution (0.55 M) and was equilibrated for 15-30 minutes on a wrist action shaker. 67 ppm of Dy(III) was stripped in the first contact, 10 ppm was stripped in the second contact, and 2 ppm was stripped in the third contact.

Similarly, from observation of the distribution ratios in FIG. 1, it is clear that heavy rare earth metals such as Tm, Yb and Lu have significantly reduced distribution factors with increasing acidity. Thus, it is also expected that heavy rare earth metals may be stripped from the ionic liquid of the present invention at relatively high pH values.

The above examples show that a large increase in the separation factors between key rare earth metal pairs may be obtained by use of an ionic liquid according to the present invention (e.g. Nd/Dy: Nd-Dy magnet, Eu/La: white lamp phosphor, Tb/Ce:green lamp phosphor). The rare earth metals may also be advantageously stripped from the ionic liquid at relatively high pH compared to prior art systems.

Without wishing to be bound by any particular theory, it is believed that a more pronounced increase in distribution ratios is observed for heavier rare earth metals than lighter rare earth metals as a result of increased formation of the more hydrophobic doubly coordinated rare earth metal species M.([MAIL$^+$][NTf$_2^-$])$_2$ over the singly coordinated species M.([MAIL$^+$][NTf$_2^-$]). It is believed that the more hydrophobic species will be more easily extracted into the organic phase during separation, leading to increased distribution ratios.

Nuclear magnetic resonance, infra-red and mass spectrometry studies have shown that the doubly coordinated species is more abundant in solutions of Lu and the ionic liquid compared to solutions of La and the ionic liquid, highlighting the differentiation between the heavy and light rare earth metals achieved by the ionic liquid of the present invention.

Furthermore, optimised geometries of the complexes LaCl$_3$.([MAIL$^+$][Cl$^-$]$^-$)$_2$ and LuCl$_3$.([MAIL$^+$][Cl$^-$]$^-$)$_2$ show that the distance between the tertiary central nitrogen of the ionic liquid cation and the metal is much longer in the case of La (~2.9 Å, non-bonding) than in the case of Lu (~2.6 Å, bonding), which also supports the weaker bonding of the ionic liquid to lighter rare earth metals. At the same time, the electron donating groups, in this case amides, linked to the nitrogen atom bond to the metal in a very similar way in both cases. This result shows that the central motif of the ionic liquid cation having a tertiary nitrogen donor is important for the differentiation obtained between the heavier and lighter rare earth metals and the improved selectivity that results therefrom.

Example 4: Liquid-Liquid Extraction of Rare Earth Metals Using [MAIL⁺][R₂P(O)O⁻]

An aqueous HCl solution containing DyCl₃·6H₂O (60 ppm Dy) and NdCl₃·6H₂O (1400 ppm Nd) at pH 1.5 was extracted with the ionic liquid extractant (0.0075 M [MAIL⁺][R₂P(O)O⁻], where R=2,4,4-trimethylpentyl, in [P₆₆₆₍₁₄₎⁺][NTf₂⁻]) according to the general procedure above. A single contact gave a SF$_{Dy\text{-}Nd}$ of 1278.

Similar experiments were conducted to compare the effect of the ionic liquid [MAIL⁺][R₂P(O)O⁻] to the ionic liquid [MAIL⁺][NTf₂⁻] at a concentration of 0.0075M in other diluents, e.g. ammonium and imidazolium ionic liquids. Improvements in both selectivity and extraction levels were observed when the phosphinate anion was used.

Similar experiments were also conducted in the presence of a phosphine (R₃P=O) and a phosphate anion [(RO)₂P(O)O⁻] in place of the phosphinate anion in the [MAIL⁺][R₂P(O)O⁻] ionic liquid. The same combination of high selectivity and high extractability was not observed.

Extraction compositions comprising [MAIL⁺][R₂P(O)O⁻], where R=2,4,4-trimethylpentyl, were prepared by combining a first ionic liquid ([P₆₆₆₍₁₄₎⁺][R₂P(O)O⁻]), a second ionic liquid ([P₆₆₆₍₁₄₎⁺][NTf₂⁻]⁻) and a third ionic liquid ([MAIL⁺][NTf₂⁻]⁻). The first and second ionic liquids were used in varying amounts to determine the optimum concentration of phosphinate anion in the composition, whilst the third ionic liquid was used at a concentration of 0.0075M. It will be appreciated that the ionic liquid [MAIL⁺][R₂P(O)O⁻] was formed in-situ in the composition.

The extraction compositions were used to selectively extract metals from an aqueous HCl solution comprising 1400 ppm Dy and 60 ppm Nd at pH 2.

| Concentration of first ionic liquid | % Extraction Nd | % Extraction Dy | Separation factor (SF) |
|---|---|---|---|
| 0.034 M | 76 | 99 | 24 |
| 0.011 M | 41 | 99 | 95 |
| 0.006 M | 30 | 97 | 84 |
| 0 | 2 | 27 | 16 |

It can be seen that high levels of extraction are achieved when the phosphinate anion is used, even when the phosphinate anion is used in a small amount. It can be seen that high levels of selectivity are also observed when the phosphinate anion is used in a concentration of from 0.005 to 0.1 M.

Example 5: Extraction of Rare Earth Metals from a Magnet Sample

A magnet sample containing rare earth metals was obtained in powdered form and was converted to the chloride form as follows. The magnet feed was dissolved in 2 M H₂SO₄. The undissolved impurities were removed by filtration. The pH was raised to 1.5 using ammonium hydroxide at 60° C. At 60° C. the rare-earth sulphates crash out of solution leaving the iron sulphate impurity in solution. The separated rare-earth sulphate was converted to the oxalate (by contacting with oxalic acid to and washing the rare-earth oxalate with water) and calcined at 900° C. to form the rare-earth oxide. The rare-earth oxide is converted into the rare-earth chloride by leaching into a HCl solution and recrystallised.

A feed solution of 0.2 g rare-earth chloride salt in 50 mL pH 2 solution (HCl) was prepared. The feed solution had an initial concentration of 20.93 ppm Dy and 1573.81 ppm Nd.

Separate extractions were carried out as described in Example 2, using 0.0075 M [MAIL⁺][NTf₂⁻] or [MAIL⁺][R₂P(O)O⁻] in [P₆₆₆₍₁₄₎⁺][NTf₂⁻] at pH 2. The ionic liquids were both found to extract more than 90% of the Dy in the solution after 4 contacts, whilst extracting less than 5% Nd.

The invention claimed is:

1. A method for extracting a rare earth metal from a mixture of one or more rare earth metals, said method comprising contacting an acidic solution of the rare earth metal with a composition which comprises an ionic liquid to form an aqueous phase and a non-aqueous phase into which the rare earth metal has been selectively extracted, wherein the ionic liquid has the formula:

[Cat⁺][X⁻]

in which:

[Cat⁺] represents a cationic species having the structure:

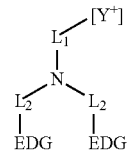

where: [Y⁺] comprises a group selected from ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium and uronium groups;

each EDG represents an electron donating group; and

L₁ represents a linking group selected from C₁₋₁₀ alkanediyl, C₂₋₁₀ alkenediyl, dialkanylether and C₁₋₁₀ dialkanylketone groups;

each L₂ represents a linking group independently selected from C₁₋₂ alkanediyl, C₂ alkenediyl, C₁₋₂ dialkanylether and C₁₋₂ dialkanylketone groups; and

[X⁻] represents a phosphinate anion.

2. The method of claim 1, wherein the method comprises recovering the rare earth metal from the non-aqueous phase, by stripping with an acidic stripping solution, wherein the acidic stripping solution has a pH of 1 or lower.

3. The method of claim 1, wherein the acidic solution comprises a first and a second rare earth metal, and the method comprises:
(a) preferentially partitioning the first rare earth metal into the non-aqueous phase.

4. The method of claim 3, wherein the method further comprises, in step (a), separating the non-aqueous phase from the acidic solution; and (b) contacting the acidic solution depleted of the first rare earth metal with the composition which comprises an ionic liquid, and recovering the second rare earth metal therefrom;

and wherein:

the first rare earth metal is recovered from the non-aqueous phase in step (a), and said non-aqueous phase is recycled and used as the composition in step (b); and the acidic solution has a pH of less than 3.5 in step (a), and the acidic solution has a pH of greater than 3.5 in step (b).

5. The method of claim 3, wherein:

the first rare earth metal is dysprosium, and the second rare earth metal is neodymium; or the first rare earth metal is europium, and the second rare earth metal is lanthanum.

6. The method of claim 1, wherein:

the acidic solution from which the rare earth metal is extracted has a pH of from 2 to 4;

the composition is added to the acidic solution in a volume ratio of from 0.5:1 to 2:1;

prior to contacting the composition with the acidic solution of the rare earth metal the composition is equilibrated with an acidic solution having the same pH as the acidic solution of the rare earth metal;

the acidic solution is contacted with the composition for from 1 to 40 minutes; and the method comprises contacting and physically mixing the acidic solution of the rare earth metal and the composition.

7. The method of claim 1, wherein when the nitrogen linking $L_1$ to each $L_2$ and one of the EDG both coordinate to a metal, the ring formed by the nitrogen, $L_2$, the EDG and the metal is a 5 or 6 membered ring.

8. The method of claim 1, wherein [Y$^+$] represents:

an acyclic cation selected from:

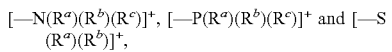

where: $R^a$, $R^b$ and $R^c$ are each selected from optionally substituted $C_{1-30}$ alkyl, $C_{3-8}$ cycloalkyl and $C_{6-10}$ aryl groups;

or a cyclic cation selected from:

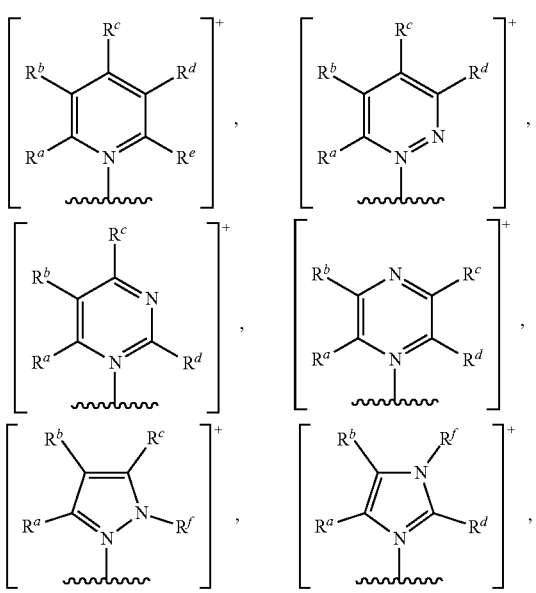

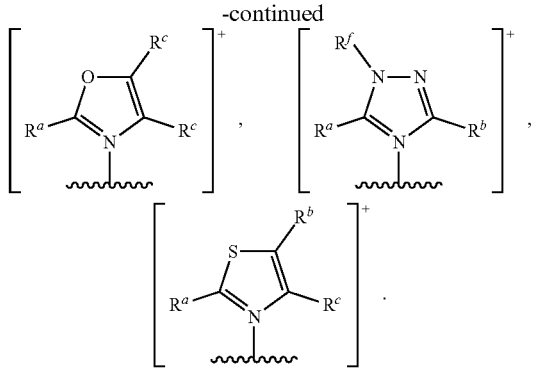

where: $R^a$, $R^b$, $R^c$, $R^d$, $R^e$ and $R^f$ are each selected from: hydrogen and substituted $C_{1-30}$ alkyl, $C_{3-8}$ cycloalkyl and $C_{6-10}$ aryl groups, or any two of $R^a$, $R^b$, $R^c$, $R^d$ and $R^e$ attached to adjacent carbon atoms form an substituted methylene chain —(CH$_2$)$_q$— where q is from 3 to 6;

or a saturated heterocyclic cation having the formula:

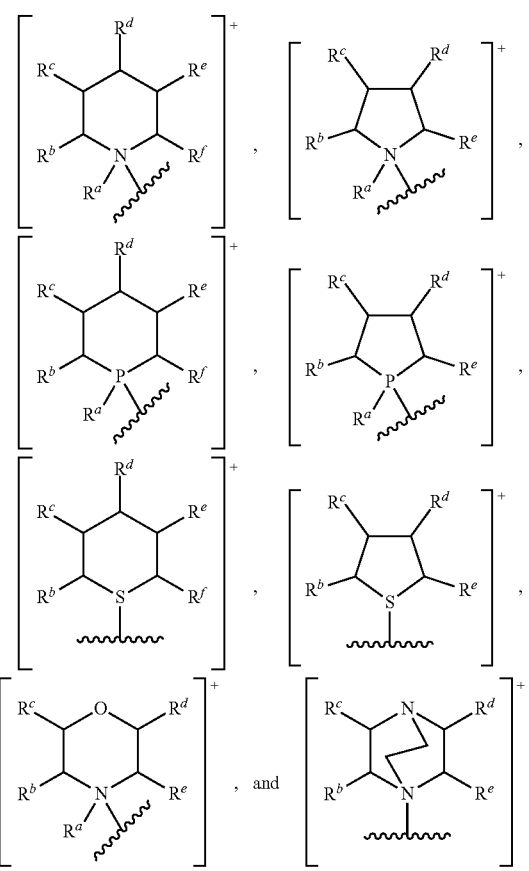

where: $R^a$, $R^b$, $R^c$, $R^d$, $R^e$ and $R^f$ are each selected from: hydrogen and substituted $C_{1-30}$ alkyl, $C_{3-8}$ cycloalkyl and $C_{6-10}$ aryl groups, or any two of $R^a$, $R^b$, $R^c$, $R^d$ and $R^e$ attached to adjacent carbon atoms form an optionally substituted methylene chain —(CH$_2$)$_q$— where q is from 3 to 6.

9. The method of claim 8, wherein [Y$^+$]0 represents a cyclic cation selected from:

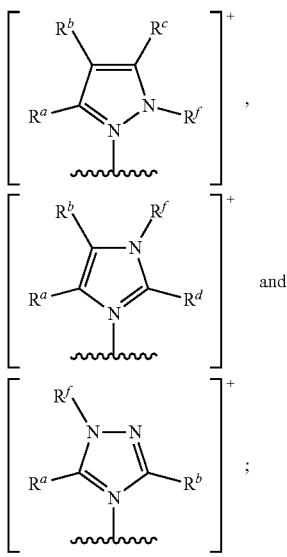

and represents the cyclic cation:

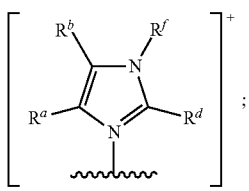

wherein $R^f$ is a substituted $C_{1-5}$ alkyl group, and the remainder of $R^a$, $R^b$, $R^c$, $R^d$, $R^e$ and $R^f$ are independently selected from H and unsubstituted $C_1$-5 alkyl groups.

10. The method of claim 1, wherein $L_1$ represents:

a linking group selected from $C_{1-10}$ alkanediyl and $C_{1-10}$ alkenediyl groups;

a linking group selected from $C_{1-5}$ alkanediyl and $C_{2-5}$ alkenediyl groups.

11. The method of claim 1, wherein each $L_2$ represents:

a linking group selected from $C_{1-2}$ alkanediyl and $C_2$ alkenediyl groups, $C_{1-2}$ alkanediyl groups, and —CH$_2$— and —C$_2$H$_4$—.

12. The method of claim 1, wherein each EDG represents:

an electron donating group independently selected from —CO$_2$R$^x$, —OC(O)R$^x$, —CS$_2$R$^x$, —SC(S)R$^x$, —S(O)OR$^x$, —OS(O) R$^x$, —NR$^x$C(O)NR$^y$R$^z$, —NR$^x$C(O)OR$^y$, —OC(O)NR$^y$N$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, wherein R$^x$, R$^y$ and R$^z$ are selected from H or $C_{1-6}$ alkyl or an electron donating group selected from —CO$_2$R$^x$ and —C(O)NR$^y$R$^z$, wherein R$^x$, R$^y$ and R$^z$ are each independently selected from $C_{3-6}$ alkyl.

13. The method of claim 12, wherein each -L$_2$-EDG represents an electron donating group selected from:

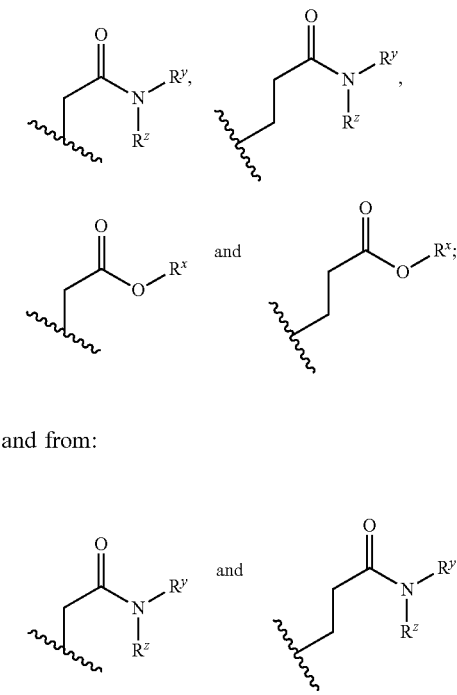

and from:

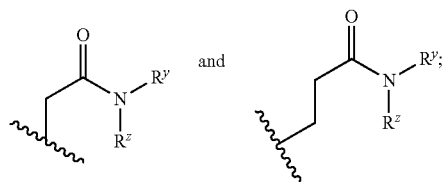

wherein $R^y$=$R^z$, and wherein $R^x$, $R^y$ and $R^z$ are each selected from $C_{3-6}$ alkyl, $C_4$ alkyl.

14. The method of claim 1, wherein [Cat$^+$] represents one or more ionic species having the structure:

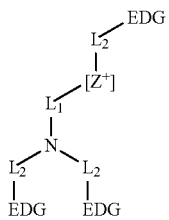

where: [Z$^+$] represents a group selected from ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium and uronium groups.

15. The method of claim 1, wherein [X$^-$] represents a phosphinate anion having the structure:

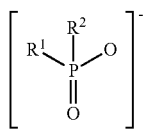

where: $R^1$ and $R^2$ are selected from optionally substituted $C_{3-20}$, $C_{4-15}$, and $C_{6-10}$, hydrocarbyl groups in which up to 3 carbon atoms may be replaced with a heteroatom.

16. The method of claim 15, wherein $R^1$ and $R^2$ are selected from alkyl, cycloalkyl, alkenyl, cycloalkenyl, alkyl-cycloalkyl, cycloalkyl-alkyl, aryl, alkyl-aryl and aryl-alkyl groups.

17. The method of claim 1, wherein the composition further comprises a lower viscosity ionic liquid and/or one or more organic solvents.

18. The method of claim 17, wherein:
the cation of the ionic liquid is present in the composition in a concentration of at least 0.001 M; and
the anion of the ionic liquid is present in the composition in a concentration of at least 0.001 M.

19. The method of claim 1, wherein the acidic solution is obtained by leaching the rare earth metal from its source using an acid, wherein the source of the rare earth metal is a mineral or a waste material.

20. A method for preparing an ionic liquid as defined in claim 1, said method comprising reacting:

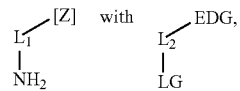

where: LG represents a leaving group,
and, where LG is not the same as X, carrying out the following reaction:

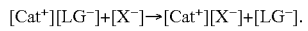

* * * * *